(12) United States Patent
Chatterton et al.

(10) Patent No.: US 9,139,834 B2
(45) Date of Patent: Sep. 22, 2015

(54) RNAI-RELATED INHIBITION OF TNF ALPHA SIGNALING PATHWAY FOR TREATMENT OF OCULAR ANGIOGENESIS

(71) Applicant: Arrowhead Research Corporation, Pasadena, CA (US)

(72) Inventors: Jon E. Chatterton, Aliso Viejo, CA (US); Abbot F. Clark, Arlington, TX (US); David P. Bingaman, Weatherford, TX (US); Martin B. Wax, Westlake, TX (US); Adrian M. Timmers, Fort Worth, TX (US)

(73) Assignee: Arrowhead Research Corporation, Pasadena, CA (US)

( * ) Notice: Subject to any disclaimer, the term of this patent is extended or adjusted under 35 U.S.C. 154(b) by 0 days.

(21) Appl. No.: 14/270,197

(22) Filed: May 5, 2014

(65) Prior Publication Data

US 2014/0357696 A1 Dec. 4, 2014

Related U.S. Application Data

(62) Division of application No. 13/169,549, filed on Jun. 27, 2011, now Pat. No. 8,754,202, which is a division of application No. 12/825,552, filed on Jun. 29, 2010, now abandoned, which is a division of application No. 12/184,351, filed on Aug. 1, 2008, now abandoned.

(60) Provisional application No. 60/953,825, filed on Aug. 3, 2007.

(51) Int. Cl.
C07H 21/04 (2006.01)
C12N 15/113 (2010.01)

(52) U.S. Cl.
CPC ........ *C12N 15/1136* (2013.01); *C12N 15/1137* (2013.01); *C12N 15/1138* (2013.01); *C12N 2310/111* (2013.01); *C12N 2310/14* (2013.01); *C12N 2310/141* (2013.01); *C12N 2310/319* (2013.01); *C12N 2310/53* (2013.01)

(58) Field of Classification Search
None
See application file for complete search history.

(56) References Cited

U.S. PATENT DOCUMENTS

| | | | |
|---|---|---|---|
| 6,531,128 B1 | 3/2003 | Wax et al. | |
| 2005/0227935 A1 | 10/2005 | McSwiggen et al. | |
| 2005/0244858 A1 | 11/2005 | Rossi et al. | 435/6 |
| 2005/0246794 A1* | 11/2005 | Khvorova et al. | 800/286 |
| 2005/0255487 A1 | 11/2005 | Khvorova et al. | 435/6 |
| 2008/0113351 A1 | 5/2008 | Naito et al. | |
| 2009/0247604 A1 | 10/2009 | Tang et al. | |
| 2009/0274626 A1 | 11/2009 | Kenny et al. | 424/9.2 |

FOREIGN PATENT DOCUMENTS

| | | |
|---|---|---|
| WO | 0158469 | 8/2001 |
| WO | 03070897 | 8/2003 |
| WO | 2007137129 | 11/2007 |

OTHER PUBLICATIONS

Black et al. (International Journal of Biochem and Cell Biol. 2002, vol. 34:1-5).
Altschul, et al., "Basic local alignment search tool"; J. Mol. Biol. vol. 215, pp. 403-410 (1990).
Campochiaro, "Potential applications for RNAi to probe pathogenesis and develop new treatments for ocular disorders"; Gene Therapy; vol. 13; pp. 559-562; (2006).
Castanotto, et al.; "Functional siRNA expression from transfected PCR products"; RNA; vol. 8; pp. 1454-1460; 2002.
Dunn, et al.; "ARPE-19, a human retinal pigment epithelial cell line with differentiated properties"; Exp. Eye Research; vol. 62, pp. 155-169, 1996.
Fontaine et al., "Neurodegenerative and neuroprotective effects of tumor necrosis factor (TNF) in retinal ischemia: opposite roles of TNF receptor 1 and TNF receptor 2"; The Journal of Neuroscience; vol. 22; pp. 1-7 (2002).
Fuchs, et al.; "Retinal-cell-conditioned medium prevents TNF-a-induced apoptosis of purified ganglion cells"; Investigative Ophthalmology & Visual Science; vol. 46, No. 8; pp. 2983-2991 Aug. 2005.
Funayama, et al.; "Variants in optineurin gene and their association with tumor necrosis factor-a polymorphisms in Japanese patients with glaucoma"; Investigative Ophthalmology & Visual Science; vol. 45, No. 12; pp. 4359-4367; Dec. 2004.
Hangai, et al.; Sequential induction of angiogenic growth factors by TNF-a in choroidal endothelial cells; Journal of Neuroimmunology; vol. 171, pp. 45-56; 2006.
Kim, et al.; "Inhibition of ocular angiogenesis by siRNA targeting vascular endothelial growth factor pathway genes"; Americal Journal of Pathology; vol. 165, No. 6; pp. 2177-2185; Dec. 2004.
Kim, et al.; "Synthetic dsRNA dicer substrates enhance RNAi potency and efficacy"; Nature Biotechnology; letters; vol. 23, No. 2, pp. 222-226; Feb. 2005.
Kociok, et al.; "Pathological but not physiological retinal neovascularization is altered in TNF-Rp55-receptor-deficient mice"; Investigative Ophthalmology & Visual Science; vol. 47, No. 11; pp. 5057-5065; Nov. 2006.
Limb et al.; "Evidence for control of tumour necrosis factor-alpha (TNF-a) activity by TNF receptors in patients with proliferative diabetic retinopathy"; Clin. Exp. Immunol.; vol. 115; pp. 409-414 (1999).
Lin, et al.; "Association of tumor necrosis factor alpha-308 gene polymorphism with primary open-angle glaucoma in Chinese"; Eye; vol. 17; pp. 31-34; 2003.
Marsh, et al; "Topical non-preserved methylprednisolone therapy for keratoconjunctivitis Sicca in Sjogren syndrome"; Ophthalmology; vol. 106, No. 4, pp. 811-816; Apr. 1999.
Pang, et al.; "Preliminary characterization of a transformed cell strain derived from human trabecular meshwork"; Current Eye Research; vol. 13, No. 1; pp. 51-63; 1994.
Picchi, et al.; "Tumor necrosis factor-a induces endothelial dysfunction in the prediabetic metabolic syndrome"; Circulation Research; pp. 69-77; Jul. 7, 2006.

(Continued)

*Primary Examiner* — Kimberly Chong

(57) ABSTRACT

RNA interference is provided for inhibition of tumor necrosis factor α (TNFα) by silencing TNFα cell surface receptor TNF receptor-1 (TNFR1) mRNA expression, or by silencing TNFα converting enzyme (TACE/ADAM17) mRNA expression. Silencing such TNFα targets, in particular, is useful for treating patients having a TNFα-related condition or at risk of developing a TNFα-related condition, such as ocular angiogenesis, retinal ischemia, and diabetic retinopathy.

17 Claims, 1 Drawing Sheet

(56) References Cited

OTHER PUBLICATIONS

Reich, et al.; "Small interfering RNA (siRNA) targeting VEGF effectively inhibits ocular neovascularization in mouse model"; Molecular Vision; vol. 9; pp. 210-216; Apr. 2003.

Saxena, et al.; "Small RNAs with imperfect match to endogenous mRNA repress translation"; Journal of Biological Chemistry; vol. 278, No. 45, pp. 44312-44319; 2003.

Shen, et al.; "Suppression of ocular neovascularization with siRNA targeting VEGF receptor 1"; Gene Therapy vol. 13; pp. 225-234; 2006.

Tezel, et al.; "Increased production of tumor necrosis factor-a by glial cells exposed to simulated ischemia or elevated hydrostatic pressure induces apoptosis in cocultured retinal ganglion cells"; The Journal of Neuroscience; vol. 20; No. 23; pp. 8693-8700; Dec. 1, 2000.

Tezel, et al.; TNF-a and TNF-a receptor-1 in the retina of normal and glaucomatous eyes; Investigative Ophthalmology & Visual Science; vol. 42, No. 8,; pp. 1787-1794; Jul. 2001.

Tschul; The siRNA user guide; Tuschel Lab; Selection of siRNA duplexes form the target mRNA sequence; p. 1-7; revised May 6, 2004.

Vinores, et al., "TNF-a is critical for ischemia-induced leukostasis, but not retinal neovascularization nor VEGF-induced leakage"; Journal of Neuroimmunology; vol. 182; pp. 73-79; 2007.

Yan, et al.; "Matrix metalloproteinases and tumor necrosis factor a in glaucomatous optic nerve head"; Arch Ophthalmol.; vol. 118; pp. 666-673; May 2000.

Yuan, et al.; Tumor necrosis factor-a: a potentially neurodestructive cytokine produced by glia in the human glaucomatous optic nerve head; GLIA, vol. 32, No. 1, pp. 42-50, Aug. 24, 2000.

Nakazawa et al.; "Tumor necrosis factor-alpha mediates oligodendrocyte death and delayed retinal ganglion cells loss in a mouse model of glaucoma"; Neurobiology of Disease; The Journal of Neuroscience; vol. 26; No. 49; pp. 12633-12641 (Dec. 6, 2006).

Tsai and Shields; "Neovascular Glaucoma"; Ophthalmology; Ocular Angiogenesis: Diseases, Mechanisms, and Therapeutics; pp. 127-147 (2006).

Xie et al.; "Harnessing in vivo siRNA delivlery for drug discovery and therapeutic development"; Drug Discovery Today; vol. 11; No. 1/2; pp. 67-73 (2006).

Bora NS et al. "Complement Activation via Alternative Pathway Is Critical in the Development of Laser-Induced Choroidal Neovascularization: Role of Factor B and Factor H" The Journal of Immunology, 2006, 177: 1872-1878.

Brummelkamp TR et al. "A System for Stable Expression of Short Interfering RNAs in Mammalian Cells" Science 2002 vol. 296, 550-553.

PCT/US2008/071885 (WO-2009-020847) International Preliminary Report on Patentability Feb. 9, 2010.

* cited by examiner

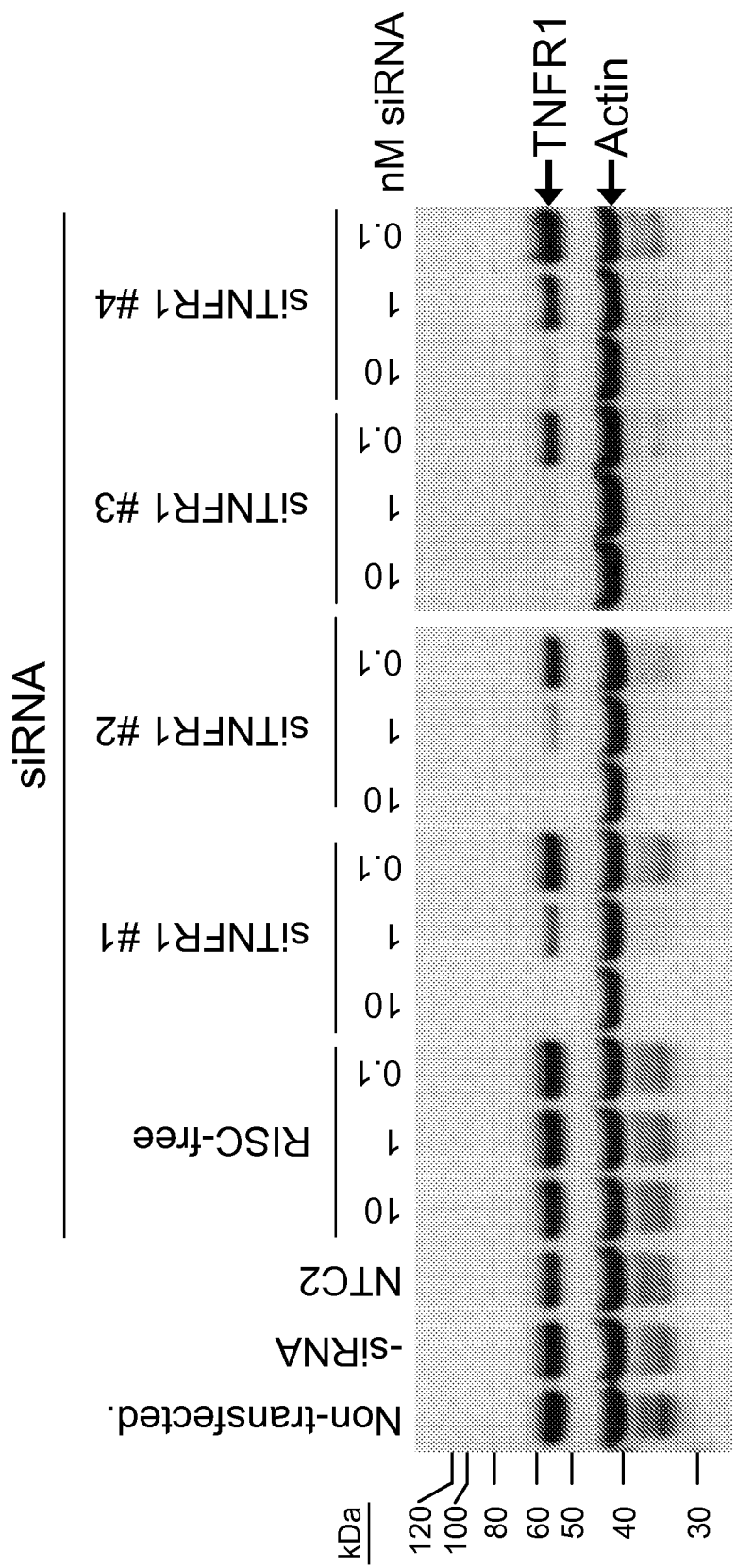

RNAI-RELATED INHIBITION OF TNF ALPHA SIGNALING PATHWAY FOR TREATMENT OF OCULAR ANGIOGENESIS

CROSS-REFERENCE TO RELATED APPLICATION

The present application is a divisional of U.S. patent application Ser. No. 13/169,549, filed Jun. 27, 2011 (now allowed), which is a divisional of U.S. patent application Ser. No. 12/825,552, filed Jun. 29, 2010 (now abandoned), which is a divisional of U.S. patent application Ser. No. 12/184,351, filed Aug. 1, 2008 (now abandoned), which claims the benefit of co-pending U.S. Provisional Patent Application Ser. No. 60/953,825 filed Aug. 3, 2007, the text of which is specifically incorporated by reference herein.

FIELD OF THE INVENTION

The present invention relates to the field of interfering RNA compositions for silencing tumor necrosis factor α (TNFα) by silencing the TNFα cell surface receptor TNF receptor-1 (TNFR1) mRNA, or the TNFα converting enzyme (TACE/ADAM17) mRNA. Silencing such TNFα targets is useful for treatment of patients having a TNFα-related condition or at risk of developing such a condition.

BACKGROUND OF THE INVENTION

Pathologic ocular neovascularization (NV) and related conditions occur as a cascade of events that progresses from an initiating stimulus to the formation of abnormal new capillaries. The stimulus appears to be the elaboration of various proangiogenic growth factors such as vascular endothelial growth factor (VEGF), platelet-derived growth factor (PDGF), and angiopoetins, among others. Following initiation of the angiogenic cascade, the capillary basement membrane and extracellular matrix are degraded and capillary endothelial cell proliferation and migration occur. Endothelial sprouts anastomose to form tubes with subsequent patent lumen formation. The new capillaries commonly have increased vascular permeability or leakiness due to immature barrier function, which can lead to tissue edema. Differentiation into a mature capillary is indicated by the presence of a continuous basement membrane and normal endothelial junctions between other endothelial cells and pericytes; however, this differentiation process is often impaired during pathologic conditions.

Retinal NV is observed in retinal ischemia, proliferative and nonproliferative diabetic retinopathy (PDR and NPDR, respectively), retinopathy of prematurity (ROP), central and branch retinal vein occlusion, and age-related macular degeneration (AMD). The retina includes choriocapillaries that form the choroid and are responsible for providing nourishment to the retina, Bruch's membrane that acts as a filter between the retinal pigment epithelium (RPE) and the choriocapillaries, and the RPE that secretes angiogenic and anti-angiogenic factors responsible for, among many other things, the growth and recession of blood vessels.

NV can include damage to Bruch's membrane which then allows growth factor to come in contact with the choriocapillaries and initiating the process of angiogenesis. The new capillaries can break through the RPE as well as Bruch's membrane to form a new vascular layer above the RPE. Leakage of the vascular layer leads to wet or exudative AMD and subsequent loss of cones and rods that are vital to vision.

Exudative AMD and PDR are the major causes of acquired blindness in developed countries and are characterized by pathologic posterior segment neovascularization (PSNV). The PSNV found in exudative AMD is characterized as pathologic choroidal NV, whereas PDR exhibits preretinal NV. In spite of the prevalence of PSNV, treatment strategies are few and palliative at best. Approved treatments for the PSNV in exudative AMD include laser photocoagulation and photodynamic therapy with VISUDYNE®; both therapies involve laser-induced occlusion of affected vasculature and are associated with localized laser-induced damage to the retina. For patients with PDR, grid or panretinal laser photocoagulation and surgical interventions, such as vitrectomy and removal of preretinal membranes, are the only options currently available. Several different compounds are being evaluated clinically for the pharmacologic treatment of PSNV, including RETAANE® (Alcon Research, Ltd.), Lucentis™, Avastin™ (Genentech), adPEDF (GenVec), squalamine (Genaera), CA4P (OxiGENE), VEGF trap (Regeneron), LY333531 (Lilly), and siRNAs targeting VEGF (CandS, Acuity) and VEGFR-1 (Sirna-027, Sirna Therapeutics). Lucentis™ (Genentech), an anti-VEGF antibody injected intravitreally, and Macugen™ (Eyetech/Pfizer), an anti-VEGF aptamer injected intravitreally, have recently been approved for such use.

Diabetes mellitus is characterized by persistent hyperglycemia that produces reversible and irreversible pathologic changes within the microvasculature of various organs. Diabetic retinopathy (DR) is a retinal microvascular disease that is manifested as a cascade of stages with increasing levels of severity and worsening prognoses for vision. Major risk factors reported for developing diabetic retinopathy include the duration of diabetes mellitus, quality of glycemic control, and presence of systemic hypertension. DR is broadly classified into 2 major clinical stages: nonproliferative diabetic retinopathy (NPDR) and proliferative diabetic retinopathy (PDR), where the term "proliferative" refers to the presence of preretinal neovascularization as previously stated. Nonproliferative diabetic retinopathy (NPDR) and subsequent macular edema are associated, in part, with retinal ischemia that results from the retinal microvasculopathy induced by persistent hyperglycemia.

Neovascularization also occurs in a type of glaucoma called neovascular glaucoma in which increased intraocular pressure is caused by growth of connective tissue and new blood vessels upon the trabecular meshwork. Neovascular glaucoma is a form of secondary glaucoma caused by neovascularization in the chamber angle.

Tumor necrosis factor α (TNFα) is a major mediator of the inflammatory response, and has been implicated in many human diseases. Binding of TNFα to its cell surface receptor, TNF receptor-1 (TNFR1), activates a signaling cascase affecting a wide variety of cellular responses, including apoptosis and inflammation. TNFα is initially expressed as an inactive, membrane-bound precursor. Release of the active form of TNFα from the cell surface requires proteolytic processing of the precursor by TNFα converting enzyme (TACE/ADAM17) Inhibiting expression of TNFR1, TACE, or both will effectively reduce the action of TNFα. It has also been reported that TNFα is involved in neovascularization and endothelial cell function (Hangei et al., 2006, *J. Neuroimmunol.* 171:45-56; and Picchi et al., 2006, *Circ. Res.* 99:69-77). In addition, Kociok et al. demonstrated that TNFR1 deficient mice exhibited reduced angiogenesis in an oxygen-induced retinopathy model (Kociok et al., 2006, *Invest. Ophthalmol. Vis. Sci.* 47:5057-5065). In contrast, Vinores et al. observed reduced leukostasis but not reduced retinal neovascularization in response to oxygen-induced retinopathy in TNFR1 deficient mice relative to wild-type mice (Vinores et al., 2006, *J. Neuroimmunol.* 182:73-79). These studies indicated that TNFα is critical for ischemia-induced leukostasis, but not retinal neovascularization or VEGF-induced leakage. Thus, interfering with the TNFα pathway may selectively block pathological neovascularization without affecting the normal process.

The present invention addresses the above-cited ocular pathologies and provides compositions and methods using interfering RNAs that target TACE and/or TNFR1 for treating neovascularization associated with retinal edema, diabetic retinopathy, sequela associated with retinal ischemia, and posterior segment neovascularization, for example. U.S. Patent Publication 2005/0227935, published Oct. 13, 2005, to McSwiggen et al. relates to RNA interference mediated inhibition of TNF and TNF receptor gene expression. However, said publication teaches none of the particular target sequences for RNA interference as provided herein.

SUMMARY OF THE INVENTION

The invention provides interfering RNAs that silence expression of TACE mRNA or TNFR1 mRNA, thus interfering with proteolytic processing of the precursor to TNFα, or interfering with binding of TNFα to its cell surface receptor, respectively, thereby attenuating activity of TNFα, and decreasing TNFR1 or TACE levels in patients with a TNFα-related ocular disorder or at risk of developing a TNFα-related ocular disorder. The interfering RNAs of the invention are useful for treating ocular angiogenesis.

The invention also provides a method of attenuating expression of a TNFR1 or TACE mRNA in a subject. In one aspect, the method comprises administering to the subject a composition comprising an effective amount of interfering RNA having a length of 19 to 49 nucleotides and a pharmaceutically acceptable carrier. In another aspect, administration is to an eye of the subject for attenuating expression of TNFR1 or TACE in a human.

In one aspect, the invention provides a method of attenuating expression of TACE mRNA in an eye of a subject, comprising administering to the eye of the subject an interfering RNA that comprises a region that can recognize a portion of mRNA corresponding to SEQ ID NO: 1, which is the sense cDNA sequence encoding TACE (GenBank Accession No. NM 003183), wherein the expression of TACE mRNA is attenuated thereby. In addition, the invention provides methods of treating an TNFα-related ocular disorder in a subject in need thereof, comprising administering to the eye of the subject an interfering RNA that comprises a region that can recognize a portion of mRNA corresponding to a portion of SEQ ID NO: 1, wherein the expression of TACE mRNA is attenuated thereby.

The invention also provides a method of attenuating expression of TNFR1 mRNA in an eye of a subject, comprising administering to the eye of the subject an interfering RNA that comprises a region that can recognize a portion of mRNA corresponding to SEQ ID NO: 2, which is the sense cDNA sequence encoding TNFR1 (GenBank Accession No. NM_001065), wherein the expression of TNFR1 mRNA is attenuated thereby. In addition, the invention provides methods of treating an TNFα-related ocular disorder in a subject in need thereof, comprising administering to the eye of the subject an interfering RNA that comprises a region that can recognize a portion of mRNA corresponding to a portion of SEQ ID NO: 2, wherein the expression of TNFR1 mRNA is attenuated thereby.

In certain aspects, an interfering RNA of the invention is designed to target an mRNA corresponding to a portion of SEQ ID NO: 1, wherein the portion comprises nucleotide 297, 333, 334, 335, 434, 470, 493, 547, 570, 573, 618, 649, 689, 755, 842, 844, 846, 860, 878, 894, 900, 909, 910, 913, 942, 970, 984, 1002, 1010, 1053, 1064, 1137, 1162, 1215, 1330, 1334, 1340, 1386, 1393, 1428, 1505, 1508, 1541, 1553, 1557, 1591, 1592, 1593, 1597, 1604, 1605, 1626, 1632, 1658, 1661, 1691, 1794, 1856, 1945, 1946, 1947, 1958, 2022, 2094, 2100, 2121, 2263, 2277, 2347, 2349, 2549, 2578, 2595, 2606, 2608, 2629, 2639, 2764, 2766, 2767, 2769, 3027, 3028, 3261, 3264, 3284, 3313, 3317, 3332, or 3337 of SEQ ID NO: 1. In particular aspects, a "portion of SEQ ID NO: 1" is about 19 to about 49 nucleotides in length.

In certain aspects, an interfering RNA of the invention is designed to target an mRNA corresponding to a portion of SEQ ID NO: 2, wherein the portion comprises nucleotide 124, 328, 387, 391, 393, 395, 406, 421, 423, 444, 447, 455, 459, 460, 467, 469, 470, 471, 475, 479, 513, 517, 531, 543, 556, 576, 587, 588, 589, 595, 601, 602, 611, 612, 651, 664, 667, 668, 669, 677, 678, 785, 786, 788, 791, 792, 804, 813, 824, 838, 843, 877, 884, 929, 959, 960, 961, 963, 964, 965, 970, 973, 974, 1000, 1002, 1013, 1026, 1053, 1056, 1057, 1058, 1161, 1315, 1318, 1324, 1357, 1360, 1383, 1393, 1420, 1471, 1573, 1671, 2044, 2045, 2046, 2047, 2048, 2089, 2090, 2091, or, 2092 of SEQ ID NO: 2. In particular aspects, a "portion of SEQ ID NO: 2" is about 19 to about 49 nucleotides in length.

In certain aspects, an interfering RNA of the invention has a length of about 19 to about 49 nucleotides. In other aspects, the interfering RNA comprises a sense nucleotide strand and an antisense nucleotide strand, wherein each strand has a region of at least near-perfect contiguous complementarity of at least 19 nucleotides with the other strand, and wherein the antisense strand can recognize (a) a portion of TACE mRNA corresponding to a portion of SEQ ID NO: 1, and has a region of at least near-perfect contiguous complementarity of at least 19 nucleotides with the portion of TACE mRNA; or (b) a portion of TNFR1 mRNA corresponding to a portion of SEQ ID NO: 2, and has a region of at least near-perfect contiguous complementarity of at least 19 nucleotides with the portion of TNFR1 mRNA. The sense and antisense strands can be connected by a linker sequence, which allows the sense and antisense strands to hybridize to each other thereby forming a hairpin loop structure as described herein.

In still other aspects, an interfering RNA of the invention is a single-stranded interfering RNA, and wherein single-stranded interfering RNA recognizes a portion of mRNA corresponding to a portion of SEQ ID NO: 1 or SEQ ID NO: 2. In certain aspects, the interfering RNA has a region of at least near-perfect contiguous complementarity of at least 19 nucleotides with the portion of mRNA corresponding to the portion of SEQ ID NO: 1 or SEQ ID NO: 2. In other aspects, the portion of SEQ ID NO: 1 comprises 297, 333, 334, 335, 434, 470, 493, 547, 570, 573, 618, 649, 689, 755, 842, 844, 846, 860, 878, 894, 900, 909, 910, 913, 942, 970, 984, 1002, 1010, 1053, 1064, 1137, 1162, 1215, 1330, 1334, 1340, 1386, 1393, 1428, 1505, 1508, 1541, 1553, 1557, 1591, 1592, 1593, 1597, 1604, 1605, 1626, 1632, 1658, 1661, 1691, 1794, 1856, 1945, 1946, 1947, 1958, 2022, 2094, 2100, 2121, 2263, 2277, 2347, 2349, 2549, 2578, 2595, 2606, 2608, 2629, 2639, 2764, 2766, 2767, 2769, 3027, 3028, 3261, 3264, 3284, 3313, 3317, 3332, or 3337 of SEQ ID NO: 1. In other aspects, the portion of SEQ ID NO: 2 comprises 124, 328, 387, 391, 393, 395, 406, 421, 423, 444, 447, 455, 459, 460, 467, 469, 470, 471, 475, 479, 513, 517, 531, 543, 556, 576, 587, 588, 589, 595, 601, 602, 611, 612, 651, 664, 667, 668, 669, 677, 678, 785, 786, 788, 791, 792, 804, 813, 824, 838, 843, 877, 884, 929, 959, 960, 961, 963, 964, 965, 970, 973, 974, 1000, 1002, 1013, 1026, 1053, 1056, 1057, 1058, 1161, 1315, 1318, 1324, 1357, 1360, 1383, 1393, 1420, 1471, 1573, 1671, 2044, 2045, 2046, 2047, 2048, 2089, 2090, 2091, or, 2092 of SEQ ID NO: 2.

In still other aspects, an interfering RNA of the invention comprises: (a) a region of at least 13 contiguous nucleotides having at least 90% sequence complementarity to, or at least 90% sequence identity with, the penultimate 13 nucleotides of the 3' end of a mRNA corresponding to any one of SEQ ID NO:3 and SEQ ID NO:14-SEQ ID NO:58; (b) a region of at least 14 contiguous nucleotides having at least 85% sequence complementarity to, or at least 85% sequence identity with, the penultimate 14 nucleotides of the 3' end of an mRNA corresponding to any one of SEQ ID NO:3 and SEQ ID NO:14-SEQ ID NO:58; or (c) a region of at least 15, 16, 17, or 18 contiguous nucleotides having at least 80% sequence complementarity to, or at least 80% sequence identity with, the penultimate 15, 16, 17, or 18 nucleotides, respectively, of the 3' end of an mRNA corresponding to any one of SEQ ID NO:3 and SEQ ID NO:14-SEQ ID NO:58; wherein the expression of the TACE mRNA is attenuated thereby.

In still other aspects, an interfering RNA of the invention comprises: (a) a region of at least 13 contiguous nucleotides having at least 90% sequence complementarity to, or at least 90% sequence identity with, the penultimate 13 nucleotides of the 3' end of a mRNA corresponding to any one of SEQ ID NO:155-SEQ ID NO:201; (b) a region of at least 14 contiguous nucleotides having at least 85% sequence complementarity to, or at least 85% sequence identity with, the penultimate 14 nucleotides of the 3' end of an mRNA corresponding to any one of SEQ ID NO:155-SEQ ID NO:201; or (c) a region of at least 15, 16, 17, or 18 contiguous nucleotides having at least 80% sequence complementarity to, or at least 80% sequence identity with, the penultimate 15, 16, 17, or 18 nucleotides, respectively, of the 3' end of an mRNA corresponding to any one of SEQ ID NO:155-SEQ ID NO:201; wherein the expression of the TNFR1 mRNA is attenuated thereby.

In further aspects, an interfering RNA of the invention or composition comprising an interfering RNA of the invention is administered to a subject via a topical, intravitreal, transcleral, periocular, conjunctival, subtenon, intracameral, subretinal, subconjunctival, retrobulbar, or intracanalicular route. The interfering RNA or composition can be administered, for example, via in vivo expression from an interfering RNA expression vector. In certain aspects, the interfering RNA or composition can be administered via an aerosol, buccal, dermal, intradermal, inhaling, intramuscular, intranasal, intraocular, intrapulmonary, intravenous, intraperitoneal, nasal, ocular, oral, otic, parenteral, patch, subcutaneous, sublingual, topical, or transdermal route.

In one aspect, an interfering RNA molecule of the invention is isolated. The term "isolated" means that the interfering RNA is free of its total natural milieu.

The invention further provides methods of treating a TNFα-related ocular disorder in a subject in need thereof, comprising administering to the subject a composition comprising a double-stranded siRNA molecule that down regulates expression of a TACE or TNFR1 gene via RNA interference, wherein each strand of the siRNA molecule is independently about 19 to about 27 nucleotides in length, and one strand of the siRNA molecule comprises a nucleotide sequence having substantial complementarity to an mRNA corresponding to the TACE or TNFR1 gene so that the siRNA molecule directs cleavage of the mRNA via RNA interference. In certain aspects, the siRNA molecule is administered via an aerosol, buccal, dermal, intradermal, inhaling, intramuscular, intranasal, intraocular, intrapulmonary, intravenous, intraperitoneal, nasal, ocular, oral, otic, parenteral, patch, subcutaneous, sublingual, topical, or transdermal route.

The invention further provides for administering a second interfering RNA to a subject in addition to a first interfering RNA. The second interfering RNA may target the same mRNA target gene as the first interfering RNA or may target a different gene. Further, a third, fourth, or fifth, etc. interfering RNA may be administered in a similar manner.

Use of any of the embodiments as described herein in the preparation of a medicament for attenuating expression of TACE or TNFR1 mRNA is also an embodiment of the present invention.

Specific preferred embodiments of the invention will become evident from the following more detailed description of certain preferred embodiments and the claims.

BRIEF DESCRIPTION OF THE FIGURES

FIG. 1 provides a TNFR1 western blot of GTM-3 cells transfected with TNFR1 siRNAs #1, #2, #3, and #4, and a RISC-free control siRNA, each at 10 nM, 1 nM, and 0.1 nM; a non-targeting control siRNA (NTC2) at 10 nM; and a buffer control (-siRNA). The arrows indicate the positions of the 55-kDa TNFR1 and 42-kDa actin bands.

DETAILED DESCRIPTION OF THE INVENTION

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, $3^{rd}$ Edition or a dictionary known to those of skill in the art, such as the Oxford Dictionary of Biochemistry and Molecular Biology (Ed. Anthony Smith, Oxford University Press, Oxford, 2004).

As used herein, all percentages are percentages by weight, unless stated otherwise.

As used herein and unless otherwise indicated, the terms "a" and "an" are taken to mean "one", "at least one" or "one or more". Unless otherwise required by context, singular terms used herein shall include pluralities and plural terms shall include the singular.

In certain embodiments, the invention provides interfering RNA molecules that can direct cleavage and/or degradation of TNFα cell surface receptor TNF receptor-1 (TNFR1) mRNA, or the TNFα converting enzyme (TACE/ADAM17, designated herein "TACE") mRNA, which inhibition effects reduction of tumor necrosis factor α (TNFα) activity, via RNA interference. Binding of TNFα to its cell surface receptor, TNF receptor-1 (TNFR1), activates a signaling cascade which affects a variety of cellular responses including apoptosis and inflammation. TNFα itself is initially expressed as an inactive, membrane-bound precursor. Release of the active form of TNFα from the cell surface requires proteolytic processing of the precursor by TNFα converting enzyme (TACE/ADAM17), a member of the 'A Disintegrin And Metalloprotease' (ADAM) family.

According to the present invention, inhibiting the expression of TNFR1 mRNA, TACE mRNA, or both TNFR1 and TACE mRNAs effectively reduces the action of TNFα. Further, interfering RNAs as set forth herein provided exogenously or expressed endogenously are particularly effective at silencing TNFR1 mRNA or TACE mRNA.

RNA interference (RNAi) is a process by which double-stranded RNA (dsRNA) is used to silence gene expression. While not wanting to be bound by theory, RNAi begins with the cleavage of longer dsRNAs into small interfering RNAs (siRNAs) by an RNaseIII-like enzyme, dicer. SiRNAs are dsRNAs that are usually about 19 to 28 nucleotides, or 20 to 25 nucleotides, or 21 to 22 nucleotides in length and often contain 2-nucleotide 3' overhangs, and 5' phosphate and 3' hydroxyl termini. One strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. Therefore, the siRNA strand that is incorporated into RISC is known as the guide strand or the antisense strand. The other siRNA strand, known as the passenger strand or the sense strand, is eliminated from the siRNA and is at least partially homologous to the target mRNA. Those of skill in the art will recognize that, in principle, either strand of an siRNA can be incorporated into RISC and function as a guide strand. However, siRNA design (e.g., decreased siRNA duplex stability at the 5' end of the desired guide strand) can favor incorporation of the desired guide strand into RISC.

The antisense strand of an siRNA is the active guiding agent of the siRNA in that the antisense strand is incorporated into RISC, thus allowing RISC to identify target mRNAs with at least partial complementarity to the antisense siRNA strand for cleavage or translational repression. RISC-related cleavage of mRNAs having a sequence at least partially complementary to the guide strand leads to a decrease in the steady state level of that mRNA and of the corresponding protein encoded by this mRNA. Alternatively, RISC can also decrease expression of the corresponding protein via translational repression without cleavage of the target mRNA.

Interfering RNAs of the invention appear to act in a catalytic manner for cleavage of target mRNA, i.e., interfering RNA is able to effect inhibition of target mRNA in substoichiometric amounts. As compared to antisense therapies, significantly less interfering RNA is required to provide a therapeutic effect under such cleavage conditions.

In certain embodiments, the invention provides methods of using interfering RNA to inhibit the expression of TACE or TNFR1 target mRNA thus decreasing TACE or TNFR1 levels in patients with a TNFα-related ocular disorder. According to the present invention, interfering RNAs provided exogenously or expressed endogenously effect silencing of TACE or TNFR1 expression in ocular tissues.

The phrase, "attenuating expression of an mRNA," as used herein, means administering or expressing an amount of interfering RNA (e.g., an siRNA) to reduce translation of the target mRNA into protein, either through mRNA cleavage or through direct inhibition of translation. The terms "inhibit," "silencing," and "attenuating" as used herein refer to a measurable reduction in expression of a target mRNA or the corresponding protein as compared with the expression of the target mRNA or the corresponding protein in the absence of an interfering RNA of the invention. The reduction in expression of the target mRNA or the corresponding protein is commonly referred to as "knock-down" and is reported relative to levels present following administration or expression of a non-targeting control RNA (e.g., a non-targeting control siRNA). Knock-down of expression of an amount including and between 50% and 100% is contemplated by embodiments herein. However, it is not necessary that such knock-down levels be achieved for purposes of the present invention.

Knock-down is commonly assessed by measuring the mRNA levels using quantitative polymerase chain reaction (qPCR) amplification or by measuring protein levels by western blot or enzyme-linked immunosorbent assay (ELISA). Analyzing the protein level provides an assessment of both mRNA cleavage as well as translation inhibition. Further techniques for measuring knock-down include RNA solution hybridization, nuclease protection, northern hybridization, gene expression monitoring with a microarray, antibody binding, radioimmunoassay, and fluorescence activated cell analysis.

Attenuating expression of TACE or TNFR1 by an interfering RNA molecule of the invention can be inferred in a human or other mammal by observing an improvement in an improvement in an ocular angiogenesis symptom such as improvement in diabetic retinopathy, retinal ischemia, or in posterior segment neovascularization (PSNV), for example.

The ability of TACE- or TNFR1-interfering RNA to knock-down the levels of TACE or TNFR1 gene expression in, for example, HeLa cells can be evaluated in vitro as follows. HeLa cells are plated 24 h prior to transfection in standard growth medium (e.g., DMEM supplemented with 10% fetal bovine serum). Transfection is performed using, for example, Dharmafect 1 (Dharmacon, Lafayette, Colo.) according to the manufacturer's instructions at interfering RNA concentrations ranging from 0.1 nM-100 nM. SiCONTROL™ Non-Targeting siRNA #1 and siCONTROL™ Cyclophilin B siRNA (Dharmacon) are used as negative and positive controls, respectively. Target mRNA levels and cyclophilin B mRNA (PPIB, NM_000942) levels are assessed by qPCR 24 h post-transfection using, for example, a TAQMAN® Gene Expression Assay that preferably overlaps the target site (Applied Biosystems, Foster City, Calif.). The positive control siRNA gives essentially complete knockdown of cyclophilin B mRNA when transfection efficiency is 100%. Therefore, target mRNA knockdown is corrected for transfection efficiency by reference to the cyclophilin B mRNA level in cells transfected with the cyclophilin B siRNA. Target protein levels may be assessed approximately 72 h post-transfection (actual time dependent on protein turnover rate) by western blot, for example. Standard techniques for RNA and/or protein isolation from cultured cells are well-known to those skilled in the art. To reduce the chance of non-specific, off-target effects, the lowest possible concentration of interfering RNA is used that produces the desired level of knock-down in target gene expression.

Human retinal pigment epithelial (RPE) cells or other human ocular cell lines may also be use for an evaluation of the ability of interfering RNA to knock-down levels of an endogenous target gene. The ability of TACE- or TNFR1-interfering RNA to knock-down the levels of endogenous TACE or TNFR1 expression in, for example, human RPE cells can be evaluated in vitro as follows. ARPE-19 cells (Dunn et al., 1996, *Exp. Eye Res.* 62:155-169) are plated 24 h prior to transfection in DMEM:F-12 medium supplemented with 10% FBS and 56 mM sodium bicarbonate and grown in 10% $CO_2$. Transfection is performed using DharmaFECT™ 1 (Dharmacon, Lafayette, Colo.) according to the manufacturer's instructions at TACE- or TNFR1-interfering RNA concentrations ranging from 0.1 nM-100 nM. Non-targeting control interfering RNA and cyclophilin B interfering RNA are used as controls. Target mRNA levels are assessed by qPCR 24 h post-transfection using, for example, TAQMAN® forward and reverse primers and a probe set that encompasses the target site (Applied Biosystems, Foster City, Calif.). Target protein levels may be assessed approximately 72 h post-transfection (actual time dependent on protein turnover rate) by western blot, for example. Standard techniques for RNA and/or protein isolation from cultured cells are well-known to those skilled in the art. To reduce the chance of non-specific, off-target effects, the lowest possible concentration of TACE- or TNFR1 interfering RNA is used that produces the desired level of knock-down in target gene expression.

A number of animal models are known that can be used to test the activity of an interfering RNA molecule of the invention. For example, siRNA molecules can be tested in murine laser-induced models of choroidal neovascularization (CNV) as described in Reich et al., 2003, *Mol. Vision* 9:210-216; Shen et al., 2006, *Gene Therapy* 13:225-234; or Bora et al., 2006, *J. Immunol.* 177:1872-1878.

In one embodiment, a single interfering RNA targeting TACE or TNFR1 mRNA is administered to decrease TACE or TNFR1 levels. In other embodiments, two or more interfering RNAs targeting the TACE and/or TNFR1 mRNA are administered to decrease TACE and/or TNFR1 levels. In certain embodiments, interfering RNA targeting TACE and interfering RNA targeting TNFR1 are administered to the subject sequentially or concurrently, thereby treating the TNFα-related ocular disease.

The GenBank database provides the DNA sequence for TACE as accession no. NM_003183, provided in the "Sequence Listing" as SEQ ID NO:1. SEQ ID NO:1 provides the sense strand sequence of DNA that corresponds to the mRNA encoding TACE (with the exception of "T" bases for "U" bases). The coding sequence for TACE is from nucleotides 184-2658.

Equivalents of the above cited TACE mRNA sequence are alternative splice forms, allelic forms, isozymes, or a cognate thereof. A cognate is a tumor necrosis factor α converting enzyme mRNA from another mammalian species that is homologous to SEQ ID NO:1 (i.e., an ortholog).

The GenBank database provides the DNA sequence for TNFR1 as accession no. NM_001065, provided in the "Sequence Listing" as SEQ ID NO:2. SEQ ID NO:2 provides the sense strand sequence of DNA that corresponds to the mRNA encoding TNFR1 (with the exception of "T" bases for "U" bases). The coding sequence for TNFR1 is from nucleotides 282-1649.

Equivalents of the above cited TNFR1 mRNA sequence are alternative splice forms, allelic forms, isozymes, or a cognate thereof. A cognate is a tumor necrosis factor receptor-1 mRNA from another mammalian species that is homologous to SEQ ID NO:2 (i.e., an ortholog).

In certain embodiments, a "subject" in need of treatment for a TNFα-related ocular disorder or at risk for developing a TNFα-related ocular disorder is a human or other mammal having a TNFα-related ocular disorder or at risk of having a TNFα-related ocular disorder associated with undesired or inappropriate expression or activity of targets as cited herein, i.e., TACE or TNFR1. Ocular structures associated with such disorders may include the eye, retina, choroid, lens, cornea, trabecular meshwork, iris, optic nerve, optic nerve head, sclera, anterior or posterior segment, or ciliary body, for example. A subject may also be an ocular cell, cell culture, organ or an ex vivo organ or tissue or cell.

"TNFα-related ocular disorder" as used herein includes conditions associated with ocular angiogenesis. The term "ocular angiogenesis," as used herein, includes ocular pre-angiogenic conditions and ocular angiogenic conditions, and includes those cellular changes resulting from the expression of TACE and/or TNFR1 mRNAs that lead directly or indirectly to ocular angiogenesis, ocular neovascularization, diabetic retinopathy, sequela associated with retinal ischemia, posterior segment neovascularization (PSNV), and neovascular glaucoma, for example. The interfering RNAs of the invention are useful for treating patients with ocular angiogenesis, ocular neovascularization, diabetic retinopathy, sequela associated with retinal ischemia, PSNV, and neovascular glaucoma, or patients at risk of developing such conditions, for example. The term "ocular neovascularization" includes age-related macular degeneration, cataract, acute ischemic optic neuropathy (AION), commotio retinae, retinal detachment, retinal tears or holes, iatrogenic retinopathy and other ischemic retinopathies or optic neuropathies, myopia, retinitis pigmentosa, and/or the like.

The term "siRNA" as used herein refers to a double-stranded interfering RNA unless otherwise noted. Typically, an siRNA of the invention is a double-stranded nucleic acid molecule comprising two nucleotide strands, each strand having about 19 to about 28 nucleotides (i.e. about 19, 20, 21, 22, 23, 24, 25, 26, 27, or 28 nucleotides). The phrase "interfering RNA having a length of 19 to 49 nucleotides" when referring to a double-stranded interfering RNA means that the anti-sense and sense strands independently have a length of about 19 to about 49 nucleotides, including interfering RNA molecules where the sense and antisense strands are connected by a linker molecule.

In addition to siRNA molecules, other interfering RNA molecules and RNA-like molecules can interact with RISC and silence gene expression. Examples of other interfering RNA molecules that can interact with RISC include short hairpin RNAs (shRNAs), single-stranded siRNAs, microRNAs (miRNAs), and dicer-substrate 27-mer duplexes. Examples of RNA-like molecules that can interact with RISC include siRNA, single-stranded siRNA, microRNA, and shRNA molecules containing one or more chemically modified nucleotides, one or more non-nucleotides, one or more deoxyribonucleotides, and/or one or more non-phosphodiester linkages. All RNA or RNA-like molecules that can interact with RISC and participate in RISC-related changes in gene expression are referred to herein as "interfering RNAs" or "interfering RNA molecules." SiRNAs, single-stranded siRNAs, shRNAs, miRNAs, and dicer-substrate 27-mer duplexes are, therefore, subsets of "interfering RNAs" or "interfering RNA molecules."

Single-stranded interfering RNA has been found to effect mRNA silencing, albeit less efficiently than double-stranded RNA. Therefore, embodiments of the present invention also provide for administration of a single-stranded interfering RNA that has a region of at least near-perfect contiguous complementarity with a portion of SEQ ID NO: 1 or a portion of SEQ ID NO: 2. The single-stranded interfering RNA has a length of about 19 to about 49 nucleotides as for the double-stranded interfering RNA cited above. The single-stranded interfering RNA has a 5' phosphate or is phosphorylated in situ or in vivo at the 5' position. The term "5' phosphorylated" is used to describe, for example, polynucleotides or oligonucleotides having a phosphate group attached via ester linkage to the C5 hydroxyl of the sugar (e.g., ribose, deoxyribose, or an analog of same) at the 5' end of the polynucleotide or oligonucleotide.

Single-stranded interfering RNAs can be synthesized chemically or by in vitro transcription or expressed endogenously from vectors or expression cassettes as described herein in reference to double-stranded interfering RNAs. 5' Phosphate groups may be added via a kinase, or a 5' phosphate may be the result of nuclease cleavage of an RNA. A hairpin interfering RNA is a single molecule (e.g., a single oligonucleotide chain) that comprises both the sense and antisense strands of an interfering RNA in a stem-loop or hairpin structure (e.g., a shRNA). For example, shRNAs can be expressed from DNA vectors in which the DNA oligonucleotides encoding a sense interfering RNA strand are linked to the DNA oligonucleotides encoding the reverse complementary antisense interfering RNA strand by a short spacer. If needed for the chosen expression vector, 3' terminal T's and nucleotides forming restriction sites may be added. The resulting RNA transcript folds back onto itself to form a stem-loop structure.

Nucleic acid sequences cited herein are written in a 5' to 3' direction unless indicated otherwise. The term "nucleic acid," as used herein, refers to either DNA or RNA or a modified form thereof comprising the purine or pyrimidine bases present in DNA (adenine "A," cytosine "C," guanine "G," thymine "T") or in RNA (adenine "A," cytosine "C," guanine "G," uracil "U"). Interfering RNAs provided herein may comprise "T" bases, particularly at 3' ends, even though "T" bases do not naturally occur in RNA. "Nucleic acid" includes the terms "oligonucleotide" and "polynucleotide" and can refer to a single-stranded molecule or a double-stranded molecule. A double-stranded molecule is formed by Watson-Crick base pairing between A and T bases, C and G bases, and between A and U bases. The strands of a double-stranded molecule may have partial, substantial or full complementarity to each other and will form a duplex hybrid, the strength of bonding of which is dependent upon the nature and degree of complementarity of the sequence of bases.

The phrase "DNA target sequence" as used herein refers to the DNA sequence that is used to derive an interfering RNA of the invention. The phrases "RNA target sequence," "interfering RNA target sequence," and "RNA target" as used herein refer to the TACE or TNFR1 mRNA or the portion of the TACE or TNFR1 mRNA sequence that can be recognized by an interfering RNA of the invention, whereby the interfering RNA can silence TACE or TNFR1 gene expression as discussed herein. An "RNA target sequence," an "siRNA target sequence," and an "RNA target" are typically mRNA sequences that correspond to a portion of a DNA sequence. An mRNA sequence is readily deduced from the sequence of the corresponding DNA sequence. For example, SEQ ID NO: 1 provides the sense strand sequence of DNA corresponding to the mRNA for TACE, while SEQ ID NO: 2 provides the sense strand sequence of DNA corresponding to the mRNA for TNFR1. The mRNA sequence is identical to the DNA sense strand sequence with the "T" bases replaced with "U" bases. Therefore, the mRNA sequence of TACE is known from SEQ ID NO: 1, and the mRNA sequence of TNFR1 is known from SEQ ID NO: 2. A target sequence in the mRNAs corresponding to SEQ ID NO: 1 or SEQ ID NO: 2 may be in the 5' or 3' untranslated regions of the mRNA as well as in the coding region of the mRNA.

In certain embodiments, interfering RNA target sequences (e.g., siRNA target sequences) within a target mRNA sequence are selected using available design tools. Interfering RNAs corresponding to a TACE or TNFR1 target sequence are then tested in vitro by transfection of cells expressing the target mRNA followed by assessment of knockdown as described herein. The interfering RNAs can be further evaluated in vivo using animal models as described herein.

Techniques for selecting target sequences for siRNAs are provided, for example, by Tuschl, T. et al., "The siRNA User Guide," revised May 6, 2004, available on the Rockefeller University web site; by Technical Bulletin #506, "siRNA Design Guidelines," Ambion Inc. at Ambion's web site; and by other web-based design tools at, for example, the Invitrogen, Dharmacon, Integrated DNA Technologies, Genscript, or Proligo web sites. Initial search parameters can include G/C contents between 35% and 55% and siRNA lengths between 19 and 27 nucleotides. The target sequence may be located in the coding region or in the 5' or 3' untranslated regions of the mRNA. The target sequences can be used to derive interfering RNA molecules, such as those described herein.

Table 1 lists examples of TACE DNA target sequences of SEQ ID NO: 1 from which interfering RNA molecules of the present invention are designed in a manner as set forth above.

TABLE 1

TACE Target Sequences for siRNAs

| TACE Target Sequence | # of Starting Nucleotide with reference to SEQ ID NO: 1 | SEQ ID NO: |
|---|---|---|
| GCTCTCAGACTACGATATT | 297 | 3 |
| CCAGCAGCATTCGGTAAGA | 333 | 14 |
| CAGCAGCATTCGGTAAGAA | 334 | 15 |
| AGCAGCATTCGGTAAGAAA | 335 | 16 |
| AGAGATCTACAGACTTCAA | 355 | 17 |
| GAAAGCGAGTACACTGTAA | 493 | 18 |
| CCATGAAGAACACGTGTAA | 842 | 19 |
| GAAGAACACGTGTAAATTA | 846 | 20 |
| ATCATCGCTTCTACAGATA | 878 | 21 |
| AGAGCAATTTAGCTTTGAT | 1137 | 22 |
| GGTTTGACGAGCACAAAGA | 1330 | 23 |
| TGATCCGGATGGTCTAGCA | 1428 | 24 |
| GCGATCACGAGAACAATAA | 1508 | 25 |
| GCAGTAAACAATCAATCTA | 1541 | 26 |
| CAATCTATAAGACCATTGA | 1553 | 27 |
| TTTCAAGAACGCAGCAATA | 1591 | 28 |
| TTCAAGAACGCAGCAATAA | 1592 | 29 |
| TCAAGAACGCAGCAATAAA | 1593 | 30 |
| TCATGTATCTGAACAACGA | 1661 | 31 |
| ACAGCGACTGCACGTTGAA | 1691 | 32 |
| GATTAATGCTACTTGCAAA | 1794 | 33 |
| CTGGAGTCCTGTGCATGTA | 1945 | 34 |
| TGGAGTCCTGTGCATGTAA | 1946 | 35 |

TABLE 1-continued

TACE Target Sequences for siRNAs

| TACE Target Sequence | # of Starting Nucleotide with reference to SEQ ID NO: 1 | SEQ ID NO: |
|---|---|---|
| GGAGTCCTGTGCATGTAAT | 1947 | 36 |
| CATGTAATGAAACTGACAA | 1958 | 37 |
| CTATGTCGATGCTGAACAA | 2022 | 38 |
| CAAATGTGAGAAACGAGTA | 2100 | 39 |
| GCATCGGTTCGCATTATCA | 2347 | 40 |
| ATCGGTTCGCATTATCAAA | 2349 | 41 |
| CCAAGTCATTTGAGGATCT | 2549 | 42 |
| CCGGTCACCAGAAGTGAAA | 2578 | 43 |
| AAAGGCTGCCTCCTTTAAA | 2595 | 44 |
| TTTAAACTGCAGCGTCAGA | 2608 | 45 |
| AGATGCTGGTCATGTGTTT | 2764 | 46 |
| ATGCTGGTCATGTGTTTGA | 2766 | 47 |
| TGCTGGTCATGTGTTTGAA | 2767 | 48 |
| CTGGTCATGTGTTTGAACT | 2769 | 49 |
| TGTAATGAACCGCTGAATA | 3027 | 50 |
| GTAATGAACCGCTGAATAT | 3028 | 51 |
| CTAAGACTAATGCTCTCTA | 3261 | 52 |
| AGACTAATGCTCTCTAGAA | 3264 | 53 |
| CCTAACCACCTACCTTACA | 3284 | 54 |
| TACATGGTAGCCAGTTGAA | 3313 | 55 |
| TGGTAGCCAGTTGAATTTA | 3317 | 56 |
| TTTATGGAATCTACCAACT | 3332 | 57 |
| GGAATCTACCAACTGTTTA | 3337 | 58 |
| CATCAAGTACTGAACGTTT | 434 | 155 |
| TCGTGGTGGTGGATGGTAA | 470 | 156 |
| GAAAGCGAGTACACTGTAA | 493 | 157 |
| GAGCCTGACTCTAGGGTTC | 547 | 158 |
| CCACATAAGAGATGATGAT | 570 | 159 |
| CATAAGAGATGATGATGTT | 573 | 160 |
| CGAATATAACATAGAGCCA | 618 | 161 |
| GTTAATGATACCAAAGACA | 649 | 162 |
| CTGAAGATATCAAGAATGT | 689 | 163 |
| ATGAAGAGTTGCTCCCAAA | 755 | 164 |
| ATGAAGAACACGTGTAAAT | 844 | 165 |
| AATTATTGGTGGTAGCAGA | 860 | 166 |
| ATCATCGCTTCTACAGATA | 878 | 167 |
| ATACATGGGCAGAGGGGAA | 894 | 168 |
| GGGCAGAGGGGAAGAGAGT | 900 | 169 |
| GGAAGAGAGTACAACTACA | 909 | 170 |
| GAAGAGAGTACAACTACAA | 910 | 171 |
| GAGAGTACAACTACAAATT | 913 | 172 |
| GCTAATTGACAGAGTTGAT | 942 | 173 |
| CGGAACACTTCATGGGATA | 970 | 174 |
| GGATAATGCAGGTTTTAAA | 984 | 175 |
| AGGCTATGGAATACAGATA | 1002 | 176 |
| GAATACAGATAGAGCAGAT | 1010 | 177 |
| GGTAAAACCTGGTGAAAAG | 1053 | 178 |
| GTGAAAAGCACTACAACAT | 1064 | 179 |
| GAGGAAGCATCTAAAGTTT | 1162 | 180 |
| TATGGGAACTCTTGGATTA | 1215 | 181 |
| TGACGAGCACAAAGAATTA | 1334 | 182 |
| GCACAAAGAATTATGGTAA | 1340 | 183 |
| GGTTACAACTCATGAATTG | 1386 | 184 |
| ACTCATGAATTGGGACATA | 1393 | 185 |
| GTGGCGATCACGAGAACAA | 1505 | 186 |
| CTATAAGACCATTGAAAGT | 1557 | 187 |
| GAACGCAGCAATAAAGTTT | 1597 | 188 |
| GCAATAAAGTTTGTGGGAA | 1604 | 189 |
| CAATAAAGTTTGTGGGAAC | 1605 | 190 |
| GAGGGTGGATGAAGGAGAA | 1626 | 191 |
| GGATGAAGGAGAAGAGTGT | 1632 | 192 |
| GCATCATGTATCTGAACAA | 1658 | 193 |
| CAGGAAATGCTGAAGATGA | 1856 | 194 |
| GAATGGCAAATGTGAGAAA | 2094 | 195 |
| GGATGTAATTGAACGATTT | 2121 | 196 |
| GTGGATAAGAAATTGGATA | 2263 | 197 |
| GGATAAACAGTATGAATCT | 2277 | 198 |
| CCTTTAAACTGCAGCGTCA | 2606 | 199 |
| CGTGTTGACAGCAAAGAAA | 2629 | 200 |
| GCAAAGAAACAGAGTGCTA | 2639 | 201 |

Table 2 lists examples of TNFR1 DNA target sequences of SEQ ID NO:2 from which siRNAs of the present invention are designed in a manner as set forth above. TNFR1 encodes tumor necrosis factor α receptor-1, as noted above.

TABLE 2

TNFR1 Target Sequences for siRNAs

| TNFR1 Target Sequence | # of Starting Nucleotide with reference to SEQ ID NO: 2 | SEQ ID NO: |
|---|---|---|
| ACCAGGCCGTGATCTCTAT | 124 | 59 |
| AATTCGATTTGCTGTACCA | 444 | 60 |
| TCGATTTGCTGTACCAAGT | 447 | 61 |
| ACAAAGGAACCTACTTGTA | 469 | 62 |
| GAACCTACTTGTACAATGA | 475 | 63 |
| CTACTTGTACAATGACTGT | 479 | 64 |
| TGTGAGAGCGGCTCCTTCA | 531 | 65 |
| TCAGGTGGAGATCTCTTCT | 611 | 66 |
| CAGGTGGAGATCTCTTCTT | 612 | 67 |
| AGAACCAGTACCGGCATTA | 667 | 68 |
| GAACCAGTACCGGCATTAT | 668 | 69 |
| AACCAGTACCGGCATTATT | 669 | 70 |
| CCGGCATTATTGGAGTGAA | 677 | 71 |
| CGGCATTATTGGAGTGAAA | 678 | 72 |
| AGCCTGGAGTGCACGAAGT | 843 | 73 |
| CTCCTCTTCATTGGTTTAA | 960 | 74 |
| TTGGTTTAATGTATCGCTA | 970 | 75 |
| GTTTAATGTATCGCTACCA | 973 | 76 |
| TTTAATGTATCGCTACCAA | 974 | 77 |
| AGTCCAAGCTCTACTCCAT | 1000 | 78 |
| GAGCTTGAAGGAACTACTA | 1053 | 79 |
| CTTGAAGGAACTACTACTA | 1056 | 80 |
| TTGAAGGAACTACTACTAA | 1057 | 81 |
| ACAAGCCACAGAGCCTAGA | 1318 | 82 |
| TGTACGCCGTGGTGGAGAA | 1357 | 83 |
| CCGTTGCGCTGGAAGGAAT | 1383 | 84 |
| TCTAAGGACCGTCCTGCGA | 1671 | 85 |
| CTAATAGAAACTTGGCACT | 2044 | 86 |
| TAATAGAAACTTGGCACTC | 2045 | 87 |
| AATAGAAACTTGGCACTCC | 2046 | 88 |
| ATAGAAACTTGGCACTCCT | 2047 | 89 |
| TAGAAACTTGGCACTCCTG | 2048 | 90 |
| ATAGCAAGCTGAACTGTCC | 2089 | 91 |
| TAGCAAGCTGAACTGTCCT | 2090 | 92 |
| AGCAAGCTGAACTGTCCTA | 2091 | 93 |
| GCAAGCTGAACTGTCCTAA | 2092 | 94 |
| TGAACTGTCCTAAGGCAGG | 2098 | 95 |
| CAAAGGAACCTACTTGTAC | 470 | 96 |
| GAGCTTGAAGGAACTACTA | 1053 | 97 |
| CACAGAGCCTAGACACTGA | 1324 | 98 |
| TCCAAGCTCTACTCCATTG | 1002 | 99 |
| TGGAGCTGTTGGTGGGAAT | 328 | 100 |
| GACAGGGAGAAGAGAGATA | 387 | 101 |
| GGGAGAAGAGAGATAGTGT | 391 | 102 |
| GAGAAGAGAGATAGTGTGT | 393 | 103 |
| GAAGAGAGATAGTGTGTGT | 395 | 104 |
| GTGTGTGTCCCCAAGGAAA | 406 | 105 |
| GAAAATATATCCACCCTCA | 421 | 106 |
| AAATATATCCACCCTCAAA | 423 | 107 |
| CTGTACCAAGTGCCACAAA | 455 | 108 |
| ACCAAGTGCCACAAAGGAA | 459 | 109 |
| CCAAGTGCCACAAAGGAAC | 460 | 110 |
| CCACAAAGGAACCTACTTG | 467 | 111 |
| CAAAGGAACCTACTTGTAC | 470 | 112 |
| AAAGGAACCTACTTGTACA | 471 | 113 |
| GATACGGACTGCAGGGAGT | 513 | 114 |
| CGGACTGCAGGGAGTGTGA | 517 | 115 |
| TCCTTCACCGCTTCAGAAA | 543 | 116 |
| CAGAAACCACCTCAGACA | 556 | 117 |
| TGCCTCAGCTGCTCCAAAT | 576 | 118 |
| CTCCAAATGCCGAAAGGAA | 587 | 119 |
| TCCAAATGCCGAAAGGAAA | 588 | 120 |
| CCAAATGCCGAAAGGAAAT | 589 | 121 |
| GCCGAAAGGAAATGGGTCA | 595 | 122 |
| AGGAAATGGGTCAGGTGGA | 601 | 123 |
| GGAAATGGGTCAGGTGGAG | 602 | 124 |
| GTGTGTGGCTGCAGGAAGA | 651 | 125 |
| GGAAGAACCAGTACCGGCA | 664 | 126 |
| CCATGCAGGTTTCTTTCTA | 785 | 127 |
| CATGCAGGTTTCTTTCTAA | 786 | 128 |
| TGCAGGTTTCTTTCTAAGA | 788 | 129 |
| AGGTTTCTTTCTAAGAGAA | 791 | 130 |
| GGTTTCTTTCTAAGAGAAA | 792 | 131 |

TABLE 2-continued

TNFR1 Target Sequences for siRNAs

| TNFR1 Target Sequence | # of Starting Nucleotide with reference to SEQ ID NO: 2 | SEQ ID NO: |
|---|---|---|
| AGAGAAAACGAGTGTGTCT | 804 | 132 |
| GAGTGTGTCTCCTGTAGTA | 813 | 133 |
| CTGTAGTAACTGTAAGAAA | 824 | 134 |
| AGAAAAGCCTGGAGTGCAC | 838 | 135 |
| TTGAGAATGTTAAGGGCAC | 877 | 136 |
| TGTTAAGGGCACTGAGGAC | 884 | 137 |
| GGTCATTTTCTTTGGTCTT | 929 | 138 |
| CCTCCTCTTCATTGGTTTA | 959 | 139 |
| TCCTCTTCATTGGTTTAAT | 961 | 140 |
| CTCTTCATTGGTTTAATGT | 963 | 141 |
| TCTTCATTGGTTTAATGTA | 964 | 142 |
| CTTCATTGGTTTAATGTAT | 965 | 143 |
| TCCAAGCTCTACTCCATTG | 1002 | 144 |
| CTCCATTGTTTGTGGGAAA | 1013 | 145 |
| GGGAAATCGACACCTGAAA | 1026 | 146 |
| TGAAGGAACTACTACTAAG | 1058 | 147 |
| ACCTCCAGCTCCACCTATA | 1161 | 148 |
| CCCACAAGCCACAGAGCCT | 1315 | 149 |
| ACGCCGTGGTGGAGAACGT | 1360 | 150 |
| GGAAGGAATTCGTGCGGCG | 1393 | 151 |
| TGAGCGACCACGAGATCGA | 1420 | 152 |
| GCGAGGCGCAATACAGCAT | 1471 | 153 |
| TGGGCTGCCTGGAGGACAT | 1573 | 154 |

As cited in the examples above, one of skill in the art is able to use the target sequence information provided in Table 1 to design interfering RNAs having a length shorter or longer than the sequences provided in Table 1 by referring to the sequence position in SEQ ID NO: 1 and adding or deleting nucleotides complementary or near complementary to SEQ ID NO: 1.

For example, SEQ ID NO: 3 represents a 19-nucleotide DNA target sequence for TACE mRNA is present at nucleotides 297 to 315 of SEQ ID NO:1:

SEQ ID NO: 3
5'-GCTCTCAGACTACGATATT-3'.

An example of an siRNA of the invention for targeting a corresponding mRNA sequence of SEQ ID NO:3 and having 21-nucleotide strands and a 2-nucleotide 3' overhang is:

SEQ ID NO: 4
5'-GCUCUCAGACUACGAUAUUNN-3'

SEQ ID NO: 5
3'-NNCGAGAGUCUGAUGCUAUAA-5'.

Each "N" residue can be any nucleotide (A, C, G, U, T) or modified nucleotide. The 3' end can have a number of "N" residues between and including 1, 2, 3, 4, 5, and 6. The "N" residues on either strand can be the same residue (e.g., UU, AA, CC, GG, or TT) or they can be different (e.g., AC, AG, AU, CA, CG, CU, GA, GC, GU, UA, UC, or UG). The 3' overhangs can be the same or they can be different. In one embodiment, both strands have a 3'UU overhang.

An example of an siRNA of the invention for targeting a corresponding mRNA sequence of SEQ ID NO:3 and having 21-nucleotide strands and a 3'UU overhang on each strand is:

SEQ ID NO: 6
5'-GCUCUCAGACUACGAUAUUUU-3'

SEQ ID NO: 7
3'-UUCGAGAGUCUGAUGCUAUAA-5'.

The interfering RNA may also have a 5' overhang of nucleotides or it may have blunt ends. An siRNA of the invention for targeting a corresponding mRNA sequence of SEQ ID NO:3 and having 19-nucleotide strands and blunt ends is:

SEQ ID NO: 8
5'-GCUCUCAGACUACGAUAUU-3'

SEQ ID NO: 9
3'-CGAGAGUCUGAUGCUAUAA-5'.

The strands of a double-stranded interfering RNA (e.g., an siRNA) may be connected to form a hairpin or stem-loop structure (e.g., an shRNA). An shRNA of the invention targeting a corresponding mRNA sequence of SEQ ID NO:3 and having a 19 by double-stranded stem region and a 3'UU overhang is:

SEQ ID NO: 10

```
                                      NNN
                                     /    \
        5'-GCUCUCAGACUACGAUAUU          N
        3'-UUCGAGAGUCUGAUGCUAUAA        N.
                                     \    /
                                      NNN
```

N is a nucleotide A, T, C, G, U, or a modified form known by one of ordinary skill in the art. The number of nucleotides N in the loop is a number between and including 3 to 23, or 5 to 15, or 7 to 13, or 4 to 9, or 9 to 11, or the number of nucleotides N is 9. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) *Science* 296: 550) and 5'-UUU-GUGUAG-3' (Castanotto, D. et al. (2002) *RNA* 8:1454). It will be recognized by one of skill in the art that the resulting single chain oligonucleotide forms a stem-loop or hairpin structure comprising a double-stranded region capable of interacting with the RNAi machinery.

The siRNA target sequence identified above can be extended at the 3' end to facilitate the design of dicer-substrate 27-mer duplexes. Extension of the 19-nucleotide DNA target sequence (SEQ ID NO:3) identified in the TACE DNA sequence (SEQ ID NO:1) by 6 nucleotides yields a 25-nucleotide DNA target sequence present at nucleotides 297 to 321 of SEQ ID NO:1:

```
                                              SEQ ID NO: 11
    5'-GCTCTCAGACTACGATATTCTCTCT-3'.
```

An example of a dicer-substrate 27-mer duplex of the invention for targeting a corresponding mRNA sequence of SEQ ID NO:11 is:

```
                                              SEQ ID NO: 12
    5'-GCUCUCAGACUACGAUAUUCUCUCU-3'

SEQ ID NO: 13
    3'-UUCGAGAGUCUGAUGCUAUAAGAGAGA-5'.
```

The two nucleotides at the 3' end of the sense strand (i.e., the CU nucleotides of SEQ ID NO:12) may be deoxynucleotides for enhanced processing. Design of dicer-substrate 27-mer duplexes from 19-21 nucleotide target sequences, such as provided herein, is further discussed by the Integrated DNA Technologies (IDT) website and by Kim, D.-H. et al., (February, 2005) *Nature Biotechnology* 23:2; 222-226.

The target RNA cleavage reaction guided by siRNAs and other forms of interfering RNA is highly sequence specific. For example, in general, an siRNA molecule contains a sense nucleotide strand identical in sequence to a portion of the target mRNA and an antisense nucleotide strand exactly complementary to a portion of the target for inhibition of mRNA expression. However, 100% sequence complementarity between the antisense siRNA strand and the target mRNA, or between the antisense siRNA strand and the sense siRNA strand, is not required to practice the present invention, so long as the interfering RNA can recognize the target mRNA and silence expression of the TACE or TNFR1 gene. Thus, for example, the invention allows for sequence variations between the antisense strand and the target mRNA and between the antisense strand and the sense strand, including nucleotide substitutions that do not affect activity of the interfering RNA molecule, as well as variations that might be expected due to genetic mutation, strain polymorphism, or evolutionary divergence, wherein the variations do not preclude recognition of the antisense strand to the target mRNA.

In one embodiment of the invention, interfering RNA of the invention has a sense strand and an antisense strand, and the sense and antisense strands comprise a region of at least near-perfect contiguous complementarity of at least 19 nucleotides. In another embodiment of the invention, an interfering RNA of the invention has a sense strand and an antisense strand, and the antisense strand comprises a region of at least near-perfect contiguous complementarity of at least 19 nucleotides to a target sequence of TACE or TNFR1 mRNA, and the sense strand comprises a region of at least near-perfect contiguous identity of at least 19 nucleotides with a target sequence of TACE or TNFR1 mRNA, respectively. In a further embodiment of the invention, the interfering RNA comprises a region of at least 13, 14, 15, 16, 17, or 18 contiguous nucleotides having percentages of sequence complementarity to or, having percentages of sequence identity with, the penultimate 13, 14, 15, 16, 17, or 18 nucleotides, respectively, of the 3' end of the corresponding target sequence within an mRNA. The length of each strand of the interfering RNA comprises about 19 to about 49 nucleotides, and may comprise a length of about 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides.

In certain embodiments, the antisense strand of an interfering RNA of the invention has at least near-perfect contiguous complementarity of at least 19 nucleotides with the target mRNA. "Near-perfect," as used herein, means the antisense strand of the siRNA is "substantially complementary to," and the sense strand of the siRNA is "substantially identical to" at least a portion of the target mRNA. "Identity," as known by one of ordinary skill in the art, is the degree of sequence relatedness between nucleotide sequences as determined by matching the order and identity of nucleotides between the sequences. In one embodiment, the antisense strand of an siRNA having 80% and between 80% up to 100% complementarity, for example, 85%, 90% or 95% complementarity, to the target mRNA sequence are considered near-perfect complementarity and may be used in the present invention. "Perfect" contiguous complementarity is standard Watson-Crick base pairing of adjacent base pairs. "At least near-perfect" contiguous complementarity includes "perfect" complementarity as used herein. Computer methods for determining identity or complementarity are designed to identify the greatest degree of matching of nucleotide sequences, for example, BLASTN (Altschul, S. F., et al. (1990) *J. Mol. Biol.* 215:403-410).

The term "percent identity" describes the percentage of contiguous nucleotides in a first nucleic acid molecule that is the same as in a set of contiguous nucleotides of the same length in a second nucleic acid molecule. The term "percent complementarity" describes the percentage of contiguous nucleotides in a first nucleic acid molecule that can base pair in the Watson-Crick sense with a set of contiguous nucleotides in a second nucleic acid molecule.

The relationship between a target mRNA and one strand of an siRNA (the sense strand) is that of identity. The sense strand of an siRNA is also called a passenger strand, if present. The relationship between a target mRNA and the other strand of an siRNA (the antisense strand) is that of complementarity. The antisense strand of an siRNA is also called a guide strand.

There may be a region or regions of the antisense siRNA strand that is (are) not complementary to a portion of SEQ ID NO: 1 or a portion of SEQ ID NO: 2. Non-complementary regions may be at the 3', 5' or both ends of a complementary region or between two complementary regions. A region can be one or more bases.

The sense and antisense strands in an interfering RNA molecule can also comprise nucleotides that do not form base pairs with the other strand. For example, one or both strands can comprise additional nucleotides or nucleotides that do not pair with a nucleotide in that position on the other strand, such that a bulge or a mismatch is formed when the strands are hybridized. Thus, an interfering RNA molecule of the invention can comprise sense and antisense strands having mismatches, G-U wobbles, or bulges. Mismatches, G-U wobbles, and bulges can also occur between the antisense strand and its target (see, for example, Saxena et al., 2003, *J. Biol. Chem.* 278:44312-9).

One or both of the strands of double-stranded interfering RNA may have a 3' overhang of from 1 to 6 nucleotides, which may be ribonucleotides or deoxyribonucleotides or a mixture thereof. The nucleotides of the overhang are not base-paired. In one embodiment of the invention, the interfering RNA comprises a 3' overhang of TT or UU. In another embodiment of the invention, the interfering RNA comprises at least one blunt end. The termini usually have a 5' phosphate group or a 3' hydroxyl group. In other embodiments, the antisense strand has a 5' phosphate group, and the sense strand has a 5' hydroxyl group. In still other embodiments, the termini are further modified by covalent addition of other molecules or functional groups.

The sense and antisense strands of the double-stranded siRNA may be in a duplex formation of two single strands as described above or may be a single-stranded molecule where the regions of complementarity are base-paired and are covalently linked by a linker molecule to form a hairpin loop when the regions are hybridized to each other. It is believed that the hairpin is cleaved intracellularly by a protein termed dicer to form an interfering RNA of two individual base-paired RNA molecules. A linker molecule can also be designed to comprise a restriction site that can be cleaved in vivo or in vitro by a particular nuclease.

In one embodiment, the invention provides an interfering RNA molecule that comprises a region of at least 13 contiguous nucleotides having at least 90% sequence complementarity to, or at least 90% sequence identity with, the penultimate 13 nucleotides of the 3' end of an mRNA corresponding to a DNA target, which allows a one nucleotide substitution within the region. Two nucleotide substitutions (i.e., 11/13=85% identity/complementarity) are not included in such a phrase. In another embodiment, the invention provides an interfering RNA molecule that comprises a region of at least 14 contiguous nucleotides having at least 85% sequence complementarity to, or at least 85% sequence identity with, the penultimate 14 nucleotides of the 3' end of an mRNA corresponding to a DNA target. Two nucleotide substitutions (i.e., 12/14=86% identity/complementarity) are included in such a phrase. In a further embodiment, the invention provides an interfering RNA molecule that comprises a region of at least 15, 16, 17, or 18 contiguous nucleotides having at least 80% sequence complementarity to, or at least 80% sequence identity with, the penultimate 14 nucleotides of the 3' end of an mRNA corresponding to a DNA target. Three nucleotide substitutions are included in such a phrase.

The penultimate base in a nucleic acid sequence that is written in a 5' to 3' direction is the next to the last base, i.e., the base next to the 3' base. The penultimate 13 bases of a nucleic acid sequence written in a 5' to 3' direction are the last 13 bases of a sequence next to the 3' base and not including the 3' base. Similarly, the penultimate 14, 15, 16, 17, or 18 bases of a nucleic acid sequence written in a 5' to 3' direction are the last 14, 15, 16, 17, or 18 bases of a sequence, respectively, next to the 3' base and not including the 3' base.

Interfering RNAs may be generated exogenously by chemical synthesis, by in vitro transcription, or by cleavage of longer double-stranded RNA with dicer or another appropriate nuclease with similar activity. Chemically synthesized interfering RNAs, produced from protected ribonucleoside phosphoramidites using a conventional DNA/RNA synthesizer, may be obtained from commercial suppliers such as Ambion Inc. (Austin, Tex.), Invitrogen (Carlsbad, Calif.), or Dharmacon (Lafayette, Colo.). Interfering RNAs can be purified by extraction with a solvent or resin, precipitation, electrophoresis, chromatography, or a combination thereof, for example. Alternatively, interfering RNA may be used with little if any purification to avoid losses due to sample processing.

When interfering RNAs are produced by chemical synthesis, phosphorylation at the 5' position of the nucleotide at the 5' end of one or both strands (when present) can enhance siRNA efficacy and specificity of the bound RISC complex, but is not required since phosphorylation can occur intracellularly.

Interfering RNAs can also be expressed endogenously from plasmid or viral expression vectors or from minimal expression cassettes, for example, PCR generated fragments comprising one or more promoters and an appropriate template or templates for the interfering RNA. Examples of commercially available plasmid-based expression vectors for shRNA include members of the pSilencer series (Ambion, Austin, Tex.) and pCpG-siRNA (InvivoGen, San Diego, Calif.). Viral vectors for expression of interfering RNA may be derived from a variety of viruses including adenovirus, adeno-associated virus, lentivirus (e.g., HIV, FIV, and EIAV), and herpes virus. Examples of commercially available viral vectors for shRNA expression include pSilencer adeno (Ambion, Austin, Tex.) and pLenti6/BLOCK-iT™-DEST (Invitrogen, Carlsbad, Calif.). Selection of viral vectors, methods for expressing the interfering RNA from the vector and methods of delivering the viral vector are within the ordinary skill of one in the art. Examples of kits for production of PCR-generated shRNA expression cassettes include Silencer Express (Ambion, Austin, Tex.) and siXpress (Mirus, Madison, Wis.).

In certain embodiments, a first interfering RNA may be administered via in vivo expression from a first expression vector capable of expressing the first interfering RNA and a second interfering RNA may be administered via in vivo expression from a second expression vector capable of expressing the second interfering RNA, or both interfering RNAs may be administered via in vivo expression from a single expression vector capable of expressing both interfering RNAs. Additional interfering RNAs can be administered in a like manner (i.e. via separate expression vectors or via a single expression vector capable of expressing multiple interfering RNAs).

Interfering RNAs may be expressed from a variety of eukaryotic promoters known to those of ordinary skill in the art, including pol III promoters, such as the U6 or H1 promoters, or pol II promoters, such as the cytomegalovirus promoter. Those of skill in the art will recognize that these promoters can also be adapted to allow inducible expression of the interfering RNA.

In certain embodiments of the present invention, an antisense strand of an interfering RNA hybridizes with an mRNA in vivo as part of the RISC complex.

"Hybridization" refers to a process in which single-stranded nucleic acids with complementary or near-complementary base sequences interact to form hydrogen-bonded complexes called hybrids. Hybridization reactions are sensitive and selective. In vitro, the specificity of hybridization (i.e., stringency) is controlled by the concentrations of salt or formamide in prehybridization and hybridization solutions, for example, and by the hybridization temperature; such procedures are well known in the art. In particular, stringency is increased by reducing the concentration of salt, increasing the concentration of formamide, or raising the hybridization temperature.

For example, high stringency conditions could occur at about 50% formamide at 37° C. to 42° C. Reduced stringency conditions could occur at about 35% to 25% formamide at 30° C. to 35° C. Examples of stringency conditions for hybridization are provided in Sambrook, J., 1989, *Molecular Cloning: A Laboratory Manual*, Cold Spring Harbor Laboratory Press, Cold Spring Harbor, N.Y. Further examples of stringent hybridization conditions include 400 mM NaCl, 40 mM PIPES pH 6.4, 1 mM EDTA, 50° C. or 70° C. for 12-16 hours followed by washing, or hybridization at 70° C. in 1×SSC or 50° C. in 1×SSC, 50% formamide followed by washing at 70° C. in 0.3×SSC, or hybridization at 70° C. in 4×SSC or 50° C. in 4×SSC, 50% formamide followed by washing at 67° C. in 1×SSC. The temperature for hybridization is about 5-10° C. less than the melting temperature ($T_m$) of the hybrid where $T_m$ is determined for hybrids between 19 and 49 base pairs in length using the following calculation: $T_m°$ C.=$81.5+16.6(\log_{10}[Na+])+0.41$ (% G+C)−(600/N)

where N is the number of bases in the hybrid, and [Na+] is the concentration of sodium ions in the hybridization buffer.

The above-described in vitro hybridization assay provides a method of predicting whether binding between a candidate siRNA and a target will have specificity. However, in the context of the RISC complex, specific cleavage of a target can also occur with an antisense strand that does not demonstrate high stringency for hybridization in vitro.

Interfering RNAs may differ from naturally-occurring RNA by the addition, deletion, substitution or modification of one or more nucleotides. Non-nucleotide material may be bound to the interfering RNA, either at the 5' end, the 3' end, or internally. Such modifications are commonly designed to increase the nuclease resistance of the interfering RNAs, to improve cellular uptake, to enhance cellular targeting, to assist in tracing the interfering RNA, to further improve stability, or to reduce the potential for activation of the interferon pathway. For example, interfering RNAs may comprise a purine nucleotide at the ends of overhangs. Conjugation of cholesterol to the 3' end of the sense strand of an siRNA molecule by means of a pyrrolidine linker, for example, also provides stability to an siRNA.

Further modifications include a 3' terminal biotin molecule, a peptide known to have cell-penetrating properties, a nanoparticle, a peptidomimetic, a fluorescent dye, or a dendrimer, for example.

Nucleotides may be modified on their base portion, on their sugar portion, or on the phosphate portion of the molecule and function in embodiments of the present invention. Modifications include substitutions with alkyl, alkoxy, amino, deaza, halo, hydroxyl, thiol groups, or a combination thereof, for example. Nucleotides may be substituted with analogs with greater stability such as replacing a ribonucleotide with a deoxyribonucleotide, or having sugar modifications such as 2' OH groups replaced by 2' amino groups, 2' O-methyl groups, 2' methoxyethyl groups, or a 2'-O, 4'-C methylene bridge, for example. Examples of a purine or pyrimidine analog of nucleotides include a xanthine, a hypoxanthine, an azapurine, a methylthioadenine, 7-deaza-adenosine and O- and N-modified nucleotides. The phosphate group of the nucleotide may be modified by substituting one or more of the oxygens of the phosphate group with nitrogen or with sulfur (phosphorothioates). Modifications are useful, for example, to enhance function, to improve stability or permeability, or to direct localization or targeting.

In certain embodiments, an interfering molecule of the invention comprises at least one of the modifications as described above.

In certain embodiments, the invention provides pharmaceutical compositions (also referred to herein as "compositions") comprising an interfering RNA molecule of the invention. Pharmaceutical compositions are formulations that comprise interfering RNAs, or salts thereof, of the invention up to 99% by weight mixed with a physiologically acceptable carrier medium, including those described infra, and such as water, buffer, saline, glycine, hyaluronic acid, mannitol, and the like.

Interfering RNAs of the present invention are administered as solutions, suspensions, or emulsions. The following are examples of pharmaceutical composition formulations that may be used in the methods of the invention.

| | Amount in weight % |
|---|---|
| Interfering RNA | up to 99; 0.1-99; 0.1-50; 0.5-10.0 |
| Hydroxypropylmethylcellulose | 0.5 |

-continued

| | Amount in weight % |
|---|---|
| Sodium chloride | 0.8 |
| Benzalkonium Chloride | 0.01 |
| EDTA | 0.01 |
| NaOH/HCl | qs pH 7.4 |
| Purified water (RNase-free) | qs 100 mL |

| | Amount in weight % |
|---|---|
| Interfering RNA | up to 99; 0.1-99; 0.1-50; 0.5-10.0 |
| Phosphate Buffered Saline | 1.0 |
| Benzalkonium Chloride | 0.01 |
| Polysorbate 80 | 0.5 |
| Purified water (RNase-free) | q.s. to 100% |

| | Amount in weight % |
|---|---|
| Interfering RNA | up to 99; 0.1-99; 0.1-50; 0.5-10.0 |
| Monobasic sodium phosphate | 0.05 |
| Dibasic sodium phosphate (anhydrous) | 0.15 |
| Sodium chloride | 0.75 |
| Disodium EDTA | 0.05 |
| Cremophor EL | 0.1 |
| Benzalkonium chloride | 0.01 |
| HCl and/or NaOH | pH 7.3-7.4 |
| Purified water (RNase-free) | q.s. to 100% |

| | Amount in weight % |
|---|---|
| Interfering RNA | up to 99; 0.1-99; 0.1-50; 0.5-10.0 |
| Phosphate Buffered Saline | 1.0 |
| Hydroxypropyl-β-cyclodextrin | 4.0 |
| Purified water (RNase-free) | q.s. to 100% |

As used herein the term "effective amount" refers to the amount of interfering RNA or a pharmaceutical composition comprising an interfering RNA determined to produce a therapeutic response in a mammal Such therapeutically effective amounts are readily ascertained by one of ordinary skill in the art and using methods as described herein.

Generally, an effective amount of the interfering RNAs of the invention results in an extracellular concentration at the surface of the target cell of from 100 pM to 1 μM, or from 1 nM to 100 nM, or from 5 nM to about 50 nM, or to about 25 nM. The dose required to achieve this local concentration will vary depending on a number of factors including the delivery method, the site of delivery, the number of cell layers between the delivery site and the target cell or tissue, whether delivery is local or systemic, etc. The concentration at the delivery site may be considerably higher than it is at the surface of the target cell or tissue. Topical compositions can be delivered to the surface of the target organ, such as the eye, one to four times per day, or on an extended delivery schedule such as daily, weekly, bi-weekly, monthly, or longer, according to the routine discretion of a skilled clinician. The pH of the formulation is about pH 4.0 to about pH 9.0, or about pH 4.5 to about pH 7.4.

An effective amount of a formulation may depend on factors such as the age, race, and sex of the subject, the rate of target gene transcript/protein turnover, the interfering RNA potency, and the interfering RNA stability, for example. In one embodiment, the interfering RNA is delivered topically to a target organ and reaches the TACE or TNFR1 mRNA-containing tissue such as the trabecular meshwork, retina or optic nerve head at a therapeutic dose thereby ameliorating TNFα-associated disease process.

Therapeutic treatment of patients with interfering RNAs directed against TACE or TNFR1 mRNA is expected to be beneficial over small molecule treatments by increasing the duration of action, thereby allowing less frequent dosing and greater patient compliance, and by increasing target specificity, thereby reducing side effects.

An "acceptable carrier" as used herein refers to those carriers that cause at most, little to no ocular irritation, provide suitable preservation if needed, and deliver one or more interfering RNAs of the present invention in a homogenous dosage. An acceptable carrier for administration of interfering RNA of embodiments of the present invention include the cationic lipid-based transfection reagents TransIT®-TKO (Mims Corporation, Madison, Wis.), LIPOFECTIN®, Lipofectamine, OLIGOFECTAMINE™ (Invitrogen, Carlsbad, Calif.), or DHARMAFECT™ (Dharmacon, Lafayette, Colo.); polycations such as polyethyleneimine; cationic peptides such as Tat, polyarginine, or Penetratin (Antp peptide); nanoparticles; or liposomes. Liposomes are formed from standard vesicle-forming lipids and a sterol, such as cholesterol, and may include a targeting molecule such as a monoclonal antibody having binding affinity for cell surface antigens, for example. Further, the liposomes may be PEGylated liposomes.

The interfering RNAs may be delivered in solution, in suspension, or in bioerodible or non-bioerodible delivery devices. The interfering RNAs can be delivered alone or as components of defined, covalent conjugates. The interfering RNAs can also be complexed with cationic lipids, cationic peptides, or cationic polymers; complexed with proteins, fusion proteins, or protein domains with nucleic acid binding properties (e.g., protamine); or encapsulated in nanoparticles or liposomes. Tissue- or cell-specific delivery can be accomplished by the inclusion of an appropriate targeting moiety such as an antibody or antibody fragment.

Interfering RNA may be delivered via aerosol, buccal, dermal, intradermal, inhaling, intramuscular, intranasal, intraocular, intrapulmonary, intravenous, intraperitoneal, nasal, ocular, oral, otic, parenteral, patch, subcutaneous, sublingual, topical, or transdermal administration, for example.

In certain embodiments, treatment of ocular disorders with interfering RNA molecules is accomplished by administration of an interfering RNA molecule directly to the eye. Local administration to the eye is advantageous for a number or reasons, including: the dose can be smaller than for systemic delivery, and there is less chance of the molecules silencing the gene target in tissues other than in the eye.

A number of studies have shown successful and effective in vivo delivery of interfering RNA molecules to the eye. For example, Kim et al. demonstrated that subconjunctival injection and systemic delivery of siRNAs targeting VEGF pathway genes inhibited angiogenesis in a mouse eye (Kim et al., 2004, *Am. J. Pathol.* 165:2177-2185). In addition, studies have shown that siRNA delivered to the vitreous cavity can diffuse throughout the eye, and is detectable up to five days after injection (Campochiaro, 2006, *Gene Therapy* 13:559-562).

Interfering RNA may be delivered directly to the eye by ocular tissue injection such as periocular, conjunctival, sub-tenon, intracameral, intravitreal, intraocular, subretinal, subconjunctival, retrobulbar, or intracanalicular injections; by direct application to the eye using a catheter or other placement device such as a retinal pellet, intraocular insert, suppository or an implant comprising a porous, non-porous, or gelatinous material; by topical ocular drops or ointments; or by a slow release device in the cul-de-sac or implanted adjacent to the sclera (transscleral) or in the sclera (intrascleral) or within the eye. Intracameral injection may be through the cornea into the anterior chamber to allow the agent to reach the trabecular meshwork. Intracanalicular injection may be into the venous collector channels draining Schlemm's canal or into Schlemm's canal.

For ophthalmic delivery, an interfering RNA may be combined with ophthalmologically acceptable preservatives, co-solvents, surfactants, viscosity enhancers, penetration enhancers, buffers, sodium chloride, or water to form an aqueous, sterile ophthalmic suspension or solution. Solution formulations may be prepared by dissolving the interfering RNA in a physiologically acceptable isotonic aqueous buffer. Further, the solution may include an acceptable surfactant to assist in dissolving the interfering RNA. Viscosity building agents, such as hydroxymethyl cellulose, hydroxyethyl cellulose, methylcellulose, polyvinylpyrrolidone, or the like may be added to the compositions of the present invention to improve the retention of the compound.

In order to prepare a sterile ophthalmic ointment formulation, the interfering RNA is combined with a preservative in an appropriate vehicle, such as mineral oil, liquid lanolin, or white petrolatum. Sterile ophthalmic gel formulations may be prepared by suspending the interfering RNA in a hydrophilic base prepared from the combination of, for example, CARBOPOL®-940 (BF Goodrich, Charlotte, N.C.), or the like, according to methods known in the art. VISCOAT® (Alcon Laboratories, Inc., Fort Worth, Tex.) may be used for intraocular injection, for example. Other compositions of the present invention may contain penetration enhancing agents such as cremephor and TWEEN® 80 (polyoxyethylene sorbitan monolaureate, Sigma Aldrich, St. Louis, Mo.), in the event the interfering RNA is less penetrating in the eye.

In certain embodiments, the invention also provides a kit that includes reagents for attenuating the expression of an mRNA as cited herein in a cell. The kit contains an siRNA or an shRNA expression vector. For siRNAs and non-viral shRNA expression vectors the kit also contains a transfection reagent or other suitable delivery vehicle. For viral shRNA expression vectors, the kit may contain the viral vector and/or the necessary components for viral vector production (e.g., a packaging cell line as well as a vector comprising the viral vector template and additional helper vectors for packaging). The kit may also contain positive and negative control siRNAs or shRNA expression vectors (e.g., a non-targeting control siRNA or an siRNA that targets an unrelated mRNA). The kit also may contain reagents for assessing knockdown of the intended target gene (e.g., primers and probes for quantitative PCR to detect the target mRNA and/or antibodies against the corresponding protein for western blots). Alternatively, the kit may comprise an siRNA sequence or an shRNA sequence and the instructions and materials necessary to generate the siRNA by in vitro transcription or to construct an shRNA expression vector.

A pharmaceutical combination in kit form is further provided that includes, in packaged combination, a carrier means adapted to receive a container means in close confinement therewith and a first container means including an interfering RNA composition and an acceptable carrier. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit.

The references cited herein, to the extent that they provide exemplary procedural or other details supplementary to those set forth herein, are specifically incorporated by reference.

Those of skill in the art, in light of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

While a particular embodiment of the invention has been shown and described, numerous variations and alternate embodiments will occur to those skilled in the art. Accordingly, the invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes to the claims that come within the meaning and range of equivalency of the claims are to be embraced within their scope. Further, all published documents, patents, and applications mentioned herein are hereby incorporated by reference, as if presented in their entirety.

EXAMPLES

The following examples, including the experiments conducted and results achieved, are provided for illustrative purposes only and are not to be construed as limiting the invention.

Example 1

Interfering RNA for Specifically Silencing TNFR1 in GTM-3 Cells

The present study examines the ability of TNFR1 interfering RNA to knock down the levels of endogenous TNFR1 protein expression in cultured GTM-3 cells.

Transfection of GTM-3 cells (Pang, I. H. et al., 1994. *Curr. Eye Res.* 13:51-63) was accomplished using standard in vitro concentrations (0.1-10 nM) of TNFR1 siRNAs, siCONTROL RISC-free siRNA, or siCONTROL Non-targeting siRNA #2 (NTC2) and DHARMAFECT® #1 transfection reagent (Dharmacon, Lafayette, Colo.). All siRNAs were dissolved in 1×siRNA buffer, an aqueous solution of 20 mM KCl, 6 mM HEPES (pH 7.5), 0.2 mM $MgCl_2$. Control samples included a buffer control in which the volume of siRNA was replaced with an equal volume of 1×siRNA buffer (-siRNA). Western blots using an anti-TNFR1 antibody (Santa Cruz Biotechnology, Santa Cruz, Calif.) were performed to assess TNFR1 protein expression. The TNFR1 siRNAs are double-stranded interfering RNAs having specificity for the following targets: siTNFR1 #1 targets the sequence CAAAGGAACCUACUUGUAC (SEQ ID NO: 202); siTNFR1 #2 targets the sequence GAGCUUGAAGGAACUACUA (SEQ ID NO: 203); siTNFR1 #3 targets the sequence CACAGAGCCUAGACACUGA (SEQ ID NO: 204); siTNFR1 #4 targets the sequence UCCAAGCUCUACUCCAUUG (SEQ ID NO: 205). As shown by the data in FIG. 1, siTNFR1 #1, siTNFR1 #2, and siTNFR1 #3 siRNAs reduced TNFR1 protein expression significantly at the 10 nM and 1 nM concentrations relative to the control siRNAs, but exhibited reduced efficacy at 0.1 nM. The siTNFR1 #2 and siTNFR1 #3 siRNAs were particularly effective. The siTNFR1 #4 siRNA also showed a concentration dependent reduction in TNFR1 protein expression as expected.

It should be understood that the foregoing disclosure emphasizes certain specific embodiments of the invention and that all modifications or alternatives equivalent thereto are within the spirit and scope of the invention as set forth in the appended claims.

---

What is claimed is:

1. A double-stranded interfering RNA molecule having a length of about 19 to about 49 nucleotides, the interfering RNA molecule comprising:
   (a) a sense strand having a region of at least 19 contiguous nucleotides corresponding to SEQ ID NO:21, except that the T's can be T's or U's; or
   (b) an antisense strand having a region of at least 19 contiguous nucleotides complementary to SEQ ID NO:21.

2. The interfering RNA molecule of claim 1 wherein the sense strand and/or the antis-sense strand contains one or more chemically modified nucleotides.

3. The interfering RNA molecule of claim 1, wherein the interfering RNA molecule has at least one blunt end.

4. The interfering RNA molecule of claim 1, wherein the interfering RNA molecule comprises a 3' overhang.

5. The interfering RNA molecule of claim 4, wherein the 3' overhang comprises about 1 to about 6 nucleotides.

6. The interfering RNA molecule of claim 5, wherein the 3' overhang comprises 2 nucleotides.

7. The interfering RNA molecule of claim 2, wherein the modified nucleotide comprises a ribose 2'-OH modification.

8. The interfering RNA molecule of claim 7, wherein the ribose 2'-OH modification is selected from the group consisting of: 2' amino group, 2' O-methyl group, 2' methoxyethyl group, and 2'-O,4'-C methylene bridge.

9. The interfering RNA molecule of claim 1, wherein a phosphate group of the nucleotide is modified by substituting one or more of the oxygens of the phosphate group with nitrogen or with sulfur.

10. The interfering RNA molecule of claim 1, wherein each strand of the double-stranded interfering RNA molecule is independently about 19 nucleotides to about 25 nucleotides in length.

11. The interfering RNA molecule of claim 10, wherein each strand of the double-stranded interfering RNA molecule is independently about 19 nucleotides to about 23 nucleotides in length.

12. The interfering RNA molecule of claim 1, wherein the interfering RNA molecule comprises a shRNA, a siRNA, or a miRNA.

13. A method of treating a TNFα-related ocular disorder in a patient in need thereof, comprising administering to the patient an interfering RNA molecule of claim 1 that attenuates expression of TACE mRNA via RNA interference, wherein the TNFα-related ocular disorder is ocular angiogenesis, ocular neovascularization, proliferative diabetic retinopathy, sequela associated with retinal ischemia, or posterior segment neovascularization (PSNV).

14. The method of claim 13, wherein the sense and antisense strands are connected by a linker to form a shRNA that can attenuate expression of TACE mRNA in a patient.

15. The method of claim 13, wherein the interfering RNA molecule is administered via in vivo expression from an expression vector capable of expressing the interfering RNA molecule.

16. The method of claim 13, wherein the patient has or is at risk of developing a TNFα-related ocular disorder.

17. The method of claim 13, wherein the interfering RNA molecule is administered via a topical, intravitreal, transcleral, periocular, conjunctival, subtenon, intracameral, subretinal, subconjunctival, retrobulbar, or intracanalicular route.

\* \* \* \* \*

UNITED STATES PATENT AND TRADEMARK OFFICE
CERTIFICATE OF CORRECTION

| | |
|---|---|
| PATENT NO. | : 9,139,834 B2 |
| APPLICATION NO. | : 14/270197 |
| DATED | : September 22, 2015 |
| INVENTOR(S) | : Jon E. Chatterton et al. |

It is certified that error appears in the above-identified patent and that said Letters Patent is hereby corrected as shown below:

Title Page (Other Publications), column 2, line 4, delete "(1990." and insert -- (1990). --.

Title Page (Other Publications), column 2, line 28, delete "Americal" and insert -- American --.

In the claims,

Column 95, line 48, claim 2, delete "antis-sense" and insert -- antisense --.

Column 96, line 47, claim 12, delete "claim 1 ," and insert -- claim 1, --.

Column 97, lines 2-3, claim 17, delete "transcleral," and insert -- transscleral, --.

Signed and Sealed this
Seventeenth Day of May, 2016

Michelle K. Lee
*Director of the United States Patent and Trademark Office*

SEQUENCE LISTING

<160> NUMBER OF SEQ ID NOS: 205

<210> SEQ ID NO 1
<211> LENGTH: 3572
<212> TYPE: DNA
<213> ORGANISM: Homo sapiens

<400> SEQUENCE: 1

```
acctgcactt ctgggggcgt cgagcctggc ggtagaatct tcccagtagg cggcgcggga      60
gggaaaagag gattgagggg ctaggccggg cggatcccgt cctcccccga tgtgagcagt     120
tttccgaaac cccgtcaggc gaaggctgcc cagagaggtg gagtcggtag cggggccggg     180
aacatgaggc agtctctcct attcctgacc agcgtggttc ctttcgtgct ggcgccgcga     240
cctccggatg acccgggctt cggcccccac cagagactcg agaagcttga ttctttgctc     300
tcagactacg atattctctc tttatctaat atccagcagc attcggtaag aaaaagagat     360
ctacagactt caacacatgt agaaacacta ctaactttt cagctttgaa aaggcatttt      420
aaattatacc tgacatcaag tactgaacgt ttttcacaaa atttcaaggt cgtggtggtg     480
gatggtaaaa acgaaagcga gtacactgta aaatggcagg acttcttcac tggacacgtg     540
```

```
gttggtgagc ctgactctag ggttctagcc cacataagag atgatgatgt tataatcaga    600
atcaacacag atggggccga atataacata gagccacttt ggagatttgt taatgatacc    660
aaagacaaaa gaatgttagt ttataaatct gaagatatca agaatgtttc acgtttgcag    720
tctccaaaag tgtgtggtta tttaaaagtg gataatgaag agttgctccc aaaagggtta    780
gtagacagag aaccacctga agagcttgtt catcgagtga aagaagagc tgacccagat    840 cccatgaaga cacgtgtaa attattggtg gtagcagatc atcgcttcta cagatacatg    900
ggcagagggg aagagagtac aactacaaat tacttaatag agctaattga cagagttgat    960
gacatctatc ggaacacttc atgggataat gcaggtttta aaggctatgg aatacagata   1020
gagcagattc gcattctcaa gtctccacaa gaggtaaaac ctggtgaaaa gcactacaac   1080
atggcaaaaa gttacccaaa tgaagaaaag gatgcttggg atgtgaagat gttgctagag   1140
caatttagct ttgatatagc tgaggaagca tctaaagttt gcttggcaca ccttttcaca   1200
taccaagatt ttgatatggg aactcttgga ttagcttatg ttggctctcc cagagcaaac   1260
agccatggag gtgtttgtcc aaaggcttat tatagcccag ttgggaagaa aaatatctat   1320
ttgaatagtg gtttgacgag cacaaagaat tatggtaaaa ccatccttac aaaggaagct   1380
gacctggtta caactcatga attgggacat aattttggag cagaacatga tccggatggt   1440
ctagcagaat gtgccccgaa tgaggaccag ggagggaaat atgtcatgta tcccatagct   1500
gtgagtggcg atcacgagaa caataagatg ttttcaaact gcagtaaaca atcaatctat   1560
aagaccattg aaagtaaggc ccaggagtgt tttcaagaac gcagcaataa agtttgtggg   1620
aactcgaggg tggatgaagg agaagagtgt gatcctggca tcatgtatct gaacaacgac   1680
acctgctgca acagcgactg cacgttgaag gaaggtgtcc agtgcagtga caggaacagt   1740
ccttgctgta aaaactgtca gtttgagact gcccagaaga gtgccagga ggcgattaat   1800 gctacttgca aaggcgtgtc ctactgcaca ggtaatagca gtgagtgccc gcctccagga   1860
aatgctgaag atgacactgt ttgcttggat cttggcaagt gtaaggatgg gaaatgcatc   1920
cctttctgcg agagggaaca gcagctggag tcctgtgcat gtaatgaaac tgacaactcc   1980
tgcaaggtgt gctgcaggga ccttctggcc gctgtgtgc cctatgtcga tgctgaacaa   2040
aagaacttat ttttgaggaa aggaaagccc tgtacagtag gattttgtga catgaatggc   2100
aaatgtgaga acagagtaca ggatgtaatt gaacgatttt gggatttcat tgaccagctg   2160
agcatcaata cttttggaaa gttttagca gacaacatcg ttgggtctgt cctggttttc   2220
tccttgatat tttggattcc tttcagcatt cttgtccatt gtgtggataa gaaattggat   2280
aaacagtatg aatctctgtc tctgtttcac cccagtaacg tcgaaatgct gagcagcatg   2340
gattctgcat cggttcgcat tatcaaaccc tttcctgcgc cccagactcc aggccgcctg   2400
cagcctgccc ctgtgatccc ttcggcgcca gcagctccaa aactggacca ccagagaatg   2460
gacaccatcc aggaagaccc cagcacagac tcacatatgg acgaggatgg gtttgagaag   2520
gaccccttcc caaatagcag cacagctgcc aagtcatttg aggatctcac ggaccatccg   2580
gtcaccagaa gtgaaaaggc tgcctccttt aaactgcagc gtcagaatcg tgttgacagc   2640
aaagaaacag agtgctaatt tagttctcag ctcttctgac ttaagtgtgc aaaatatttt   2700
tatagatttg acctacaaat caatcacagc ttgtatttttg tgaagactgg gaagtgactt   2760
agcagatgct ggtcatgtgt ttgaacttcc tgcaggtaaa cagttcttgt gtggtttggc   2820
ccttctcctt tgaaaaggt aaggtgaagg tgaatctagc ttattttgag gctttcaggt   2880
tttagttttt aaaatatctt ttgacctgtg gtgcaaaagc agaaaataca gctggattgg   2940
```

-continued

| | | |
|---|---|---|
| gttatgaata tttacgtttt tgtaaattaa tcttttatat tgataacagc actgactagg | 3000 |
| gaaatgatca gttttttttt atacactgta atgaaccgct gaatatgagg catttggcat | 3060 |
| ttatttgtga tgacaactgg aatagttttt tttttttttt ttttttttttg ccttcaacta | 3120 |
| aaaacaaagg agataaatct agtatacatt gtctctaaat tgtgggtcta tttctagtta | 3180 |
| ttacccagag ttttatgta gcagggaaaa tatatatcta aatttagaaa tcatttgggt | 3240 |
| taatatggct cttcataatt ctaagactaa tgctctctag aaacctaacc acctaccttta | 3300 |
| cagtgagggc tatacatggt agccagttga atttatggaa tctaccaact gtttagggcc | 3360 |
| ctgatttgct gggcagtttt tctgtatttt ataagtatct tcatgtatcc ctgttactga | 3420 |
| tagggataca tgctcttaga aaattcacta ttggctggga gtggtggctc atgcctgtaa | 3480 |
| tcccagcact tggagaggct gaggttgcgc cactacactc cagcctgggt gacagagtga | 3540 |
| gactctgcct caaaaaaaaa aaaaaaaaaa aa | 3572 |

<210> SEQ ID NO 2
<211> LENGTH: 2236
<212> TYPE: DNA
<213> ORGANISM: Homo sapiens

<400> SEQUENCE: 2

| | | |
|---|---|---|
| gctgttgcaa cactgcctca ctcttcccct cccaccttct ctcccctcct ctctgcttta | 60 |
| attttctcag aattctctgg actgaggctc cagttctggc ctttggggtt caagatcact | 120 |
| gggaccaggc cgtgatctct atgcccgagt ctcaaccctc aactgtcacc ccaaggcact | 180 |
| tgggacgtcc tggacagacc gagtcccggg aagccccagc actgccgctg ccacactgcc | 240 |
| ctgagcccaa atgggggagt gagaggccat agctgtctgg catgggcctc tccaccgtgc | 300 |
| ctgacctgct gctgccactg gtgctcctgg agctgttggt gggaatatac ccctcagggg | 360 |
| ttattggact ggtccctcac ctaggggaca gggagaagag agatagtgtg tgtccccaag | 420 |
| gaaaatatat ccaccctcaa aataattcga tttgctgtac caagtgccac aaaggaacct | 480 |
| acttgtacaa tgactgtcca ggcccggggc aggatacgga ctgcagggag tgtgagagcg | 540 |
| gctccttcac cgcttcagaa aaccacctca gacactgcct cagctgctcc aaatgccgaa | 600 |
| aggaaatggg tcaggtggag atctcttctt gcacagtgga ccgggacacc gtgtgtggct | 660 |
| gcaggaagaa ccagtaccgg cattattgga gtgaaaacct tttccagtgc ttcaattgca | 720 |
| gcctctgcct caatgggacc gtgcacctct cctgccagga gaaacagaac accgtgtgca | 780 |
| cctgccatgc aggtttcttt ctaagagaaa acgagtgtgt ctcctgtagt aactgtaaga | 840 |
| aaagcctgga gtgcacgaag ttgtgcctac ccagattgaa gaatgttaag ggcactgagg | 900 |
| actcaggcac cacagtgctg ttgcccctgg tcattttctt tggtctttgc cttttatccc | 960 |
| tcctcttcat tggtttaatg tatcgctacc aacggtggaa gtccaagctc tactccattg | 1020 |
| tttgtgggaa atcgacacct gaaaagaggg ggagcttga aggaactact actaagcccc | 1080 |
| tggccccaaa cccaagcttc agtcccactc caggcttcac cccacccctg gcttcagtc | 1140 |
| ccgtgcccag ttccaccttc acctccagct ccacctatac cccggtgac tgtcccaact | 1200 |
| tgcggctcc ccgcagagag gtggcaccac cctatcaggg gctgaccccc atccttgcga | 1260 |
| cagccctcgc ctccgacccc atccccaacc cccttcagaa gtgggaggac agcgcccaca | 1320 |
| agccacagag cctagacact gatgacccg cgacgctgta cgccgtggtg gagaacgtgc | 1380 |
| ccccgttgcg ctggaaggaa ttcgtgcggc gcctagggct gagcgaccac gagatcgatc | 1440 |

```
ggctggagct gcagaacggg cgctgcctgc gcgaggcgca atacagcatg ctggcgacct    1500
ggaggcggcg cacgccgcgg cgcgaggcca cgctggagct gctgggacgc gtgctccgcg    1560
acatggacct gctgggctgc ctggaggaca tcgaggaggc gctttgcggc cccgccgccc    1620
tcccgcccgc gcccagtctt tcagatgag gctgcgcccc tgcggcagc tctaaggacc      1680 gtcctgcgag atcgccttcc aaccccactt ttttctggaa aggaggggtc ctgcaggggc    1740
aagcaggagc tagcagccgc ctacttggtg ctaacccctc gatgtacata gcttttctca    1800
gctgcctgcg cgccgccgac agtcagcgct gtgcgcgcgg agagaggtgc gccgtgggct    1860
caagagcctg agtgggtggt ttgcgaggat gagggacgct atgcctcatg cccgttttgg    1920
gtgtcctcac cagcaaggct gctcgggggc ccctggttcg tccctgagcc ttttcacag     1980 tgcataagca gttttttttg tttttgtttt gttttgtttt gttttttaaat caatcatgtt    2040 acactaatag aaacttggca ctcctgtgcc ctctgcctgg acaagcacat agcaagctga    2100
actgtcctaa ggcaggggcg agcacggaac aatggggcct tcagctggag ctgtggactt    2160
ttgtacatac actaaaattc tgaagttaaa gctctgctct tggaaaaaaa aaaaaaaaaa    2220
aaaaaaaaaa aaaaaa                                                    2236

<210> SEQ ID NO 3
<211> LENGTH: 19
<212> TYPE: DNA
<213> ORGANISM: Artificial
<220> FEATURE:
<223> OTHER INFORMATION: Target Sequence

<400> SEQUENCE: 3
gctctcagac tacgatatt                                                 19

<210> SEQ ID NO 4
<211> LENGTH: 21
<212> TYPE: DNA
<213> ORGANISM: Artificial
<220> FEATURE:
<223> OTHER INFORMATION: Sense Strand with 3'NN
<220> FEATURE:
<221> NAME/KEY: misc_RNA
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: any, A, T/U, C, G

<400> SEQUENCE: 4
gcucucagac uacgauauun n                                              21

<210> SEQ ID NO 5
<211> LENGTH: 21
<212> TYPE: DNA
<213> ORGANISM: Artificial
<220> FEATURE:
<223> OTHER INFORMATION: Antisense strand with 3'NN
<220> FEATURE:
<221> NAME/KEY: misc_RNA
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: any, A, T/U, C, G

<400> SEQUENCE: 5
aauaucguag ucugagagcn n                                              21
```

```
<210> SEQ ID NO 6
<211> LENGTH: 21
<212> TYPE: RNA
<213> ORGANISM: Artificial
<220> FEATURE:
<223> OTHER INFORMATION: Sense Strand

<400> SEQUENCE: 6
gcucucagac uacgauauuu u                                              21

<210> SEQ ID NO 7
<211> LENGTH: 21
<212> TYPE: RNA
<213> ORGANISM: Artificial
<220> FEATURE:
<223> OTHER INFORMATION: Antisense Strand

<400> SEQUENCE: 7
aauaucguag ucugagagcu u                                              21

<210> SEQ ID NO 8
<211> LENGTH: 19
<212> TYPE: RNA
<213> ORGANISM: Artificial
<220> FEATURE:
<223> OTHER INFORMATION: Sense Strand

<400> SEQUENCE: 8
gcucucagac uacgauauu                                                 19

<210> SEQ ID NO 9
<211> LENGTH: 19
<212> TYPE: RNA
<213> ORGANISM: Artificial
<220> FEATURE:
<223> OTHER INFORMATION: Antisense Strand

<400> SEQUENCE: 9
aauaucguag ucugagagc                                                 19

<210> SEQ ID NO 10
<211> LENGTH: 48
<212> TYPE: DNA
<213> ORGANISM: Artificial
<220> FEATURE:
<223> OTHER INFORMATION: Hairpin duplex with loop
<220> FEATURE:
<221> NAME/KEY: misc_RNA
<222> LOCATION: (1)..(19)
<223> OTHER INFORMATION: ribonucleotides
<220> FEATURE:
<221> NAME/KEY: misc_feature
<222> LOCATION: (20)..(27)
<223> OTHER INFORMATION: any, A, T/U, C, G
<220> FEATURE:
<221> NAME/KEY: misc_feature
<222> LOCATION: (28)..(48)
<223> OTHER INFORMATION: ribonucleotides

<400> SEQUENCE: 10
gcucucagac uacgauauun nnnnnnaau aucguagucu gagagcuu                  48

<210> SEQ ID NO 11
<211> LENGTH: 25
<212> TYPE: DNA
<213> ORGANISM: Artificial
<220> FEATURE:
```

<223> OTHER INFORMATION: Sense Strand

<400> SEQUENCE: 11
gcucucagac uacgauauuc ucucu                                      25

<210> SEQ ID NO 12
<211> LENGTH: 25
<212> TYPE: RNA
<213> ORGANISM: Artificial
<220> FEATURE:
<223> OTHER INFORMATION: Sense Strand

<400> SEQUENCE: 12
gcucucagac uacgauauuc ucucu                                      25

<210> SEQ ID NO 13
<211> LENGTH: 27
<212> TYPE: RNA
<213> ORGANISM: Artificial
<220> FEATURE:
<223> OTHER INFORMATION: Antisense Strand

<400> SEQUENCE: 13
agagagaaua ucguagucug agagcuu                                    27

<210> SEQ ID NO 14
<211> LENGTH: 19
<212> TYPE: DNA
<213> ORGANISM: Artificial
<220> FEATURE:
<223> OTHER INFORMATION: Target Sequence

<400> SEQUENCE: 14
ccagcagcat tcggtaaga                                             19

<210> SEQ ID NO 15
<211> LENGTH: 19
<212> TYPE: DNA
<213> ORGANISM: Artificial
<220> FEATURE:
<223> OTHER INFORMATION: Target Sequence

<400> SEQUENCE: 15
cagcagcatt cggtaagaa                                             19

<210> SEQ ID NO 16
<211> LENGTH: 19
<212> TYPE: DNA
<213> ORGANISM: Artificial
<220> FEATURE:
<223> OTHER INFORMATION: Target Sequence

<400> SEQUENCE: 16
agcagcattc ggtaagaaa                                             19

<210> SEQ ID NO 17
<211> LENGTH: 19
<212> TYPE: DNA
<213> ORGANISM: Artificial
<220> FEATURE:
<223> OTHER INFORMATION: Target Sequence

<400> SEQUENCE: 17
agagatctac agacttcaa                                             19

```
<210> SEQ ID NO 18
<211> LENGTH: 19
<212> TYPE: DNA
<213> ORGANISM: Artificial
<220> FEATURE:
<223> OTHER INFORMATION: Target Sequence

<400> SEQUENCE: 18
gaaagcgagt acactgtaa                                                    19

<210> SEQ ID NO 19
<211> LENGTH: 19
<212> TYPE: DNA
<213> ORGANISM: Artificial
<220> FEATURE:
<223> OTHER INFORMATION: Target Sequence

<400> SEQUENCE: 19
ccatgaagaa cacgtgtaa                                                    19

<210> SEQ ID NO 20
<211> LENGTH: 19
<212> TYPE: DNA
<213> ORGANISM: Artificial
<220> FEATURE:
<223> OTHER INFORMATION: Target Sequence

<400> SEQUENCE: 20
gaagaacacg tgtaaatta                                                    19

<210> SEQ ID NO 21
<211> LENGTH: 19
<212> TYPE: DNA
<213> ORGANISM: Artificial
<220> FEATURE:
<223> OTHER INFORMATION: Target Sequence

<400> SEQUENCE: 21
atcatcgctt ctacagata                                                    19

<210> SEQ ID NO 22
<211> LENGTH: 19
<212> TYPE: DNA
<213> ORGANISM: Artificial
<220> FEATURE:
<223> OTHER INFORMATION: Target Sequence

<400> SEQUENCE: 22
agagcaattt agctttgat                                                    19

<210> SEQ ID NO 23
<211> LENGTH: 19
<212> TYPE: DNA
<213> ORGANISM: Artificial
<220> FEATURE:
<223> OTHER INFORMATION: Target Sequence

<400> SEQUENCE: 23
ggtttgacga gcacaaaga                                                    19

<210> SEQ ID NO 24
<211> LENGTH: 19
<212> TYPE: DNA
<213> ORGANISM: Artificial
<220> FEATURE:
<223> OTHER INFORMATION: Target Sequence
```

```
<400> SEQUENCE: 24
tgatccggat ggtctagca                                                19

<210> SEQ ID NO 25
<211> LENGTH: 19
<212> TYPE: DNA
<213> ORGANISM: Artificial
<220> FEATURE:
<223> OTHER INFORMATION: Target Sequence

<400> SEQUENCE: 25
gcgatcacga gaacaataa                                                19

<210> SEQ ID NO 26
<211> LENGTH: 19
<212> TYPE: DNA
<213> ORGANISM: Artificial
<220> FEATURE:
<223> OTHER INFORMATION: Target Sequence

<400> SEQUENCE: 26
gcagtaaaca atcaatcta                                                19

<210> SEQ ID NO 27
<211> LENGTH: 19
<212> TYPE: DNA
<213> ORGANISM: Artificial
<220> FEATURE:
<223> OTHER INFORMATION: Target Sequence

<400> SEQUENCE: 27
caatctataa gaccattga                                                19

<210> SEQ ID NO 28
<211> LENGTH: 19
<212> TYPE: DNA
<213> ORGANISM: Artificial
<220> FEATURE:
<223> OTHER INFORMATION: Target Sequence

<400> SEQUENCE: 28
tttcaagaac gcagcaata                                                19

<210> SEQ ID NO 29
<211> LENGTH: 19
<212> TYPE: DNA
<213> ORGANISM: Artificial
<220> FEATURE:
<223> OTHER INFORMATION: Target Sequence

<400> SEQUENCE: 29
ttcaagaacg cagcaataa                                                19

<210> SEQ ID NO 30
<211> LENGTH: 19
<212> TYPE: DNA
<213> ORGANISM: Artificial
<220> FEATURE:
<223> OTHER INFORMATION: Target Sequence

<400> SEQUENCE: 30
tcaagaacgc agcaataaa                                                19

<210> SEQ ID NO 31
<211> LENGTH: 19
```

```
<212> TYPE: DNA
<213> ORGANISM: Artificial
<220> FEATURE:
<223> OTHER INFORMATION: Target Sequence

<400> SEQUENCE: 31
tcatgtatct gaacaacga                                                  19

<210> SEQ ID NO 32
<211> LENGTH: 19
<212> TYPE: DNA
<213> ORGANISM: Artificial
<220> FEATURE:
<223> OTHER INFORMATION: Target Sequence

<400> SEQUENCE: 32
acagcgactg cacgttgaa                                                  19

<210> SEQ ID NO 33
<211> LENGTH: 19
<212> TYPE: DNA
<213> ORGANISM: Artificial
<220> FEATURE:
<223> OTHER INFORMATION: Target Sequence

<400> SEQUENCE: 33
gattaatgct acttgcaaa                                                  19

<210> SEQ ID NO 34
<211> LENGTH: 19
<212> TYPE: DNA
<213> ORGANISM: Artificial
<220> FEATURE:
<223> OTHER INFORMATION: Target Sequence

<400> SEQUENCE: 34
ctggagtcct gtgcatgta                                                  19

<210> SEQ ID NO 35
<211> LENGTH: 19
<212> TYPE: DNA
<213> ORGANISM: Artificial
<220> FEATURE:
<223> OTHER INFORMATION: Target Sequence

<400> SEQUENCE: 35
tggagtcctg tgcatgtaa                                                  19

<210> SEQ ID NO 36
<211> LENGTH: 19
<212> TYPE: DNA
<213> ORGANISM: Artificial
<220> FEATURE:
<223> OTHER INFORMATION: Target Sequence

<400> SEQUENCE: 36
ggagtcctgt gcatgtaat                                                  19

<210> SEQ ID NO 37
<211> LENGTH: 19
<212> TYPE: DNA
<213> ORGANISM: Artificial
<220> FEATURE:
<223> OTHER INFORMATION: Target Sequence

<400> SEQUENCE: 37
```
catgtaatga aactgacaa                                                  19

<210> SEQ ID NO 38
<211> LENGTH: 19
<212> TYPE: DNA
<213> ORGANISM: Artificial
<220> FEATURE:
<223> OTHER INFORMATION: Target Sequence

<400> SEQUENCE: 38
ctatgtcgat gctgaacaa                                                  19

<210> SEQ ID NO 39
<211> LENGTH: 19
<212> TYPE: DNA
<213> ORGANISM: Artificial
<220> FEATURE:
<223> OTHER INFORMATION: Target Sequence

<400> SEQUENCE: 39
caaatgtgag aaacgagta                                                  19

<210> SEQ ID NO 40
<211> LENGTH: 19
<212> TYPE: DNA
<213> ORGANISM: Artificial
<220> FEATURE:
<223> OTHER INFORMATION: Target Sequence

<400> SEQUENCE: 40
gcatcggttc gcattatca                                                  19

<210> SEQ ID NO 41
<211> LENGTH: 19
<212> TYPE: DNA
<213> ORGANISM: Artificial
<220> FEATURE:
<223> OTHER INFORMATION: Target Sequence

<400> SEQUENCE: 41
atcggttcgc attatcaaa                                                  19

<210> SEQ ID NO 42
<211> LENGTH: 19
<212> TYPE: DNA
<213> ORGANISM: Artificial
<220> FEATURE:
<223> OTHER INFORMATION: Target Sequence

<400> SEQUENCE: 42
ccaagtcatt tgaggatct                                                  19

<210> SEQ ID NO 43
<211> LENGTH: 19
<212> TYPE: DNA
<213> ORGANISM: Artificial
<220> FEATURE:
<223> OTHER INFORMATION: Target Sequence

<400> SEQUENCE: 43
ccggtcacca gaagtgaaa                                                  19

<210> SEQ ID NO 44
<211> LENGTH: 19
<212> TYPE: DNA
<213> ORGANISM: Artificial

```
<220> FEATURE:
<223> OTHER INFORMATION: Target Sequence

<400> SEQUENCE: 44
aaaggctgcc tcctttaaa                                                    19

<210> SEQ ID NO 45
<211> LENGTH: 19
<212> TYPE: DNA
<213> ORGANISM: Artificial
<220> FEATURE:
<223> OTHER INFORMATION: Target Sequence

<400> SEQUENCE: 45
tttaaactgc agcgtcaga                                                    19

<210> SEQ ID NO 46
<211> LENGTH: 19
<212> TYPE: DNA
<213> ORGANISM: Artificial
<220> FEATURE:
<223> OTHER INFORMATION: Target Sequence

<400> SEQUENCE: 46
agatgctggt catgtgttt                                                    19

<210> SEQ ID NO 47
<211> LENGTH: 19
<212> TYPE: DNA
<213> ORGANISM: Artificial
<220> FEATURE:
<223> OTHER INFORMATION: Target Sequence

<400> SEQUENCE: 47
atgctggtca tgtgtttga                                                    19

<210> SEQ ID NO 48
<211> LENGTH: 19
<212> TYPE: DNA
<213> ORGANISM: Artificial
<220> FEATURE:
<223> OTHER INFORMATION: Target Sequence

<400> SEQUENCE: 48
tgctggtcat gtgtttgaa                                                    19

<210> SEQ ID NO 49
<211> LENGTH: 19
<212> TYPE: DNA
<213> ORGANISM: Artificial
<220> FEATURE:
<223> OTHER INFORMATION: Target Sequence

<400> SEQUENCE: 49
ctggtcatgt gtttgaact                                                    19

<210> SEQ ID NO 50
<211> LENGTH: 19
<212> TYPE: DNA
<213> ORGANISM: Artificial
<220> FEATURE:
<223> OTHER INFORMATION: Target Sequence

<400> SEQUENCE: 50
tgtaatgaac cgctgaata                                                    19
```

<210> SEQ ID NO 51
<211> LENGTH: 19
<212> TYPE: DNA
<213> ORGANISM: Artificial
<220> FEATURE:
<223> OTHER INFORMATION: Target Sequence

<400> SEQUENCE: 51
gtaatgaacc gctgaatat                                            19

<210> SEQ ID NO 52
<211> LENGTH: 19
<212> TYPE: DNA
<213> ORGANISM: Artificial
<220> FEATURE:
<223> OTHER INFORMATION: Target Sequence

<400> SEQUENCE: 52
ctaagactaa tgctctcta                                            19

<210> SEQ ID NO 53
<211> LENGTH: 19
<212> TYPE: DNA
<213> ORGANISM: Artificial
<220> FEATURE:
<223> OTHER INFORMATION: Target Sequence

<400> SEQUENCE: 53
agactaatgc tctctagaa                                            19

<210> SEQ ID NO 54
<211> LENGTH: 19
<212> TYPE: DNA
<213> ORGANISM: Artificial
<220> FEATURE:
<223> OTHER INFORMATION: Target Sequence

<400> SEQUENCE: 54
cctaaccacc taccttaca                                            19

<210> SEQ ID NO 55
<211> LENGTH: 19
<212> TYPE: DNA
<213> ORGANISM: Artificial
<220> FEATURE:
<223> OTHER INFORMATION: Target Sequence

<400> SEQUENCE: 55
tacatggtag ccagttgaa                                            19

<210> SEQ ID NO 56
<211> LENGTH: 19
<212> TYPE: DNA
<213> ORGANISM: Artificial
<220> FEATURE:
<223> OTHER INFORMATION: Target Sequence

<400> SEQUENCE: 56
tggtagccag ttgaattta                                            19

<210> SEQ ID NO 57
<211> LENGTH: 19
<212> TYPE: DNA
<213> ORGANISM: Artificial
<220> FEATURE:
<223> OTHER INFORMATION: Target Sequence

<400> SEQUENCE: 57
tttatggaat ctaccaact                                                    19

<210> SEQ ID NO 58
<211> LENGTH: 19
<212> TYPE: DNA
<213> ORGANISM: Artificial
<220> FEATURE:
<223> OTHER INFORMATION: Target Sequence

<400> SEQUENCE: 58
ggaatctacc aactgttta                                                    19

<210> SEQ ID NO 59
<211> LENGTH: 19
<212> TYPE: DNA
<213> ORGANISM: Artificial
<220> FEATURE:
<223> OTHER INFORMATION: Target Sequence

<400> SEQUENCE: 59
accaggccgt gatctctat                                                    19

<210> SEQ ID NO 60
<211> LENGTH: 19
<212> TYPE: DNA
<213> ORGANISM: Artificial
<220> FEATURE:
<223> OTHER INFORMATION: Target Sequence

<400> SEQUENCE: 60
aattcgattt gctgtacca                                                    19

<210> SEQ ID NO 61
<211> LENGTH: 19
<212> TYPE: DNA
<213> ORGANISM: Artificial
<220> FEATURE:
<223> OTHER INFORMATION: Target Sequence

<400> SEQUENCE: 61
tcgatttgct gtaccaagt                                                    19

<210> SEQ ID NO 62
<211> LENGTH: 19
<212> TYPE: DNA
<213> ORGANISM: Artificial
<220> FEATURE:
<223> OTHER INFORMATION: Target Sequence

<400> SEQUENCE: 62
acaaaggaac ctacttgta                                                    19

<210> SEQ ID NO 63
<211> LENGTH: 19
<212> TYPE: DNA
<213> ORGANISM: Artificial
<220> FEATURE:
<223> OTHER INFORMATION: Target Sequence

<400> SEQUENCE: 63
gaacctactt gtacaatga                                                    19

<210> SEQ ID NO 64

```
<211> LENGTH: 19
<212> TYPE: DNA
<213> ORGANISM: Artificial
<220> FEATURE:
<223> OTHER INFORMATION: Target Sequence

<400> SEQUENCE: 64
ctacttgtac aatgactgt                                                      19

<210> SEQ ID NO 65
<211> LENGTH: 19
<212> TYPE: DNA
<213> ORGANISM: Artificial
<220> FEATURE:
<223> OTHER INFORMATION: Target Sequence

<400> SEQUENCE: 65
tgtgagagcg gctccttca                                                      19

<210> SEQ ID NO 66
<211> LENGTH: 19
<212> TYPE: DNA
<213> ORGANISM: Artificial
<220> FEATURE:
<223> OTHER INFORMATION: Target Sequence

<400> SEQUENCE: 66
tcaggtggag atctcttct                                                      19

<210> SEQ ID NO 67
<211> LENGTH: 19
<212> TYPE: DNA
<213> ORGANISM: Artificial
<220> FEATURE:
<223> OTHER INFORMATION: Target Sequence

<400> SEQUENCE: 67
caggtggaga tctcttctt                                                      19

<210> SEQ ID NO 68
<211> LENGTH: 19
<212> TYPE: DNA
<213> ORGANISM: Artificial
<220> FEATURE:
<223> OTHER INFORMATION: Target Sequence

<400> SEQUENCE: 68
agaaccagta ccggcatta                                                      19

<210> SEQ ID NO 69
<211> LENGTH: 19
<212> TYPE: DNA
<213> ORGANISM: Artificial
<220> FEATURE:
<223> OTHER INFORMATION: Target Sequence

<400> SEQUENCE: 69
gaaccagtac cggcattat                                                      19

<210> SEQ ID NO 70
<211> LENGTH: 19
<212> TYPE: DNA
<213> ORGANISM: Artificial
<220> FEATURE:
<223> OTHER INFORMATION: Target Sequence

<400> SEQUENCE: 70
```
aaccagtacc ggcattatt                                                19

<210> SEQ ID NO 71
<211> LENGTH: 19
<212> TYPE: DNA
<213> ORGANISM: Artificial
<220> FEATURE:
<223> OTHER INFORMATION: Target Sequence

<400> SEQUENCE: 71
ccggcattat tggagtgaa                                                19

<210> SEQ ID NO 72
<211> LENGTH: 19
<212> TYPE: DNA
<213> ORGANISM: Artificial
<220> FEATURE:
<223> OTHER INFORMATION: Target Sequence

<400> SEQUENCE: 72
cggcattatt ggagtgaaa                                                19

<210> SEQ ID NO 73
<211> LENGTH: 19
<212> TYPE: DNA
<213> ORGANISM: Artificial
<220> FEATURE:
<223> OTHER INFORMATION: Target Sequence

<400> SEQUENCE: 73
agcctggagt gcacgaagt                                                19

<210> SEQ ID NO 74
<211> LENGTH: 19
<212> TYPE: DNA
<213> ORGANISM: Artificial
<220> FEATURE:
<223> OTHER INFORMATION: Target Sequence

<400> SEQUENCE: 74
ctcctcttca ttggttaa                                                 19

<210> SEQ ID NO 75
<211> LENGTH: 19
<212> TYPE: DNA
<213> ORGANISM: Artificial
<220> FEATURE:
<223> OTHER INFORMATION: Target Sequence

<400> SEQUENCE: 75
ttggtttaat gtatcgcta                                                19

<210> SEQ ID NO 76
<211> LENGTH: 19
<212> TYPE: DNA
<213> ORGANISM: Artificial
<220> FEATURE:
<223> OTHER INFORMATION: Target Sequence

<400> SEQUENCE: 76
gtttaatgta tcgctacca                                                19

<210> SEQ ID NO 77
<211> LENGTH: 19
<212> TYPE: DNA

```
<213> ORGANISM: Artificial
<220> FEATURE:
<223> OTHER INFORMATION: Target Sequence

<400> SEQUENCE: 77
tttaatgtat cgctaccaa                                                19

<210> SEQ ID NO 78
<211> LENGTH: 19
<212> TYPE: DNA
<213> ORGANISM: Artificial
<220> FEATURE:
<223> OTHER INFORMATION: Target Sequence

<400> SEQUENCE: 78
agtccaagct ctactccat                                                19

<210> SEQ ID NO 79
<211> LENGTH: 19
<212> TYPE: DNA
<213> ORGANISM: Artificial
<220> FEATURE:
<223> OTHER INFORMATION: Target Sequence

<400> SEQUENCE: 79
gagcttgaag gaactacta                                                19

<210> SEQ ID NO 80
<211> LENGTH: 19
<212> TYPE: DNA
<213> ORGANISM: Artificial
<220> FEATURE:
<223> OTHER INFORMATION: Target Sequence

<400> SEQUENCE: 80
cttgaaggaa ctactacta                                                19

<210> SEQ ID NO 81
<211> LENGTH: 19
<212> TYPE: DNA
<213> ORGANISM: Artificial
<220> FEATURE:
<223> OTHER INFORMATION: Target Sequence

<400> SEQUENCE: 81
ttgaaggaac tactactaa                                                19

<210> SEQ ID NO 82
<211> LENGTH: 19
<212> TYPE: DNA
<213> ORGANISM: Artificial
<220> FEATURE:
<223> OTHER INFORMATION: Target Sequence

<400> SEQUENCE: 82
acaagccaca gagcctaga                                                19

<210> SEQ ID NO 83
<211> LENGTH: 19
<212> TYPE: DNA
<213> ORGANISM: Artificial
<220> FEATURE:
<223> OTHER INFORMATION: Target Sequence

<400> SEQUENCE: 83
tgtacgccgt ggtggagaa                                                19
```

```
<210> SEQ ID NO 84
<211> LENGTH: 19
<212> TYPE: DNA
<213> ORGANISM: Artificial
<220> FEATURE:
<223> OTHER INFORMATION: Target Sequence

<400> SEQUENCE: 84
ccgttgcgct ggaaggaat                                                  19

<210> SEQ ID NO 85
<211> LENGTH: 19
<212> TYPE: DNA
<213> ORGANISM: Artificial
<220> FEATURE:
<223> OTHER INFORMATION: Target Sequence

<400> SEQUENCE: 85
tctaaggacc gtcctgcga                                                  19

<210> SEQ ID NO 86
<211> LENGTH: 19
<212> TYPE: DNA
<213> ORGANISM: Artificial
<220> FEATURE:
<223> OTHER INFORMATION: Target Sequence

<400> SEQUENCE: 86
ctaatagaaa cttggcact                                                  19

<210> SEQ ID NO 87
<211> LENGTH: 19
<212> TYPE: DNA
<213> ORGANISM: Artificial
<220> FEATURE:
<223> OTHER INFORMATION: Target Sequence

<400> SEQUENCE: 87
taatagaaac ttggcactc                                                  19

<210> SEQ ID NO 88
<211> LENGTH: 19
<212> TYPE: DNA
<213> ORGANISM: Artificial
<220> FEATURE:
<223> OTHER INFORMATION: Target Sequence

<400> SEQUENCE: 88
aatagaaact tggcactcc                                                  19

<210> SEQ ID NO 89
<211> LENGTH: 19
<212> TYPE: DNA
<213> ORGANISM: Artificial
<220> FEATURE:
<223> OTHER INFORMATION: Target Sequence

<400> SEQUENCE: 89
atagaaactt ggcactcct                                                  19

<210> SEQ ID NO 90
<211> LENGTH: 19
<212> TYPE: DNA
<213> ORGANISM: Artificial
<220> FEATURE:
```

<223> OTHER INFORMATION: Target Sequence

<400> SEQUENCE: 90
tagaaacttg gcactcctg                                                    19

<210> SEQ ID NO 91
<211> LENGTH: 19
<212> TYPE: DNA
<213> ORGANISM: Artificial
<220> FEATURE:
<223> OTHER INFORMATION: Target Sequence

<400> SEQUENCE: 91
atagcaagct gaactgtcc                                                    19

<210> SEQ ID NO 92
<211> LENGTH: 19
<212> TYPE: DNA
<213> ORGANISM: Artificial
<220> FEATURE:
<223> OTHER INFORMATION: Target Sequence

<400> SEQUENCE: 92
tagcaagctg aactgtcct                                                    19

<210> SEQ ID NO 93
<211> LENGTH: 19
<212> TYPE: DNA
<213> ORGANISM: Artificial
<220> FEATURE:
<223> OTHER INFORMATION: Target Sequence

<400> SEQUENCE: 93
agcaagctga actgtccta                                                    19

<210> SEQ ID NO 94
<211> LENGTH: 19
<212> TYPE: DNA
<213> ORGANISM: Artificial
<220> FEATURE:
<223> OTHER INFORMATION: Target Sequence

<400> SEQUENCE: 94
gcaagctgaa ctgtcctaa                                                    19

<210> SEQ ID NO 95
<211> LENGTH: 19
<212> TYPE: DNA
<213> ORGANISM: Artificial
<220> FEATURE:
<223> OTHER INFORMATION: Target Sequence

<400> SEQUENCE: 95
tgaactgtcc taaggcagg                                                    19

<210> SEQ ID NO 96
<211> LENGTH: 19
<212> TYPE: DNA
<213> ORGANISM: Artificial
<220> FEATURE:
<223> OTHER INFORMATION: Target Sequence

<400> SEQUENCE: 96
caaaggaacc tacttgtac                                                    19

```
<210> SEQ ID NO 97
<211> LENGTH: 19
<212> TYPE: DNA
<213> ORGANISM: Artificial
<220> FEATURE:
<223> OTHER INFORMATION: Target Sequence

<400> SEQUENCE: 97
gagcttgaag gaactacta                                                    19

<210> SEQ ID NO 98
<211> LENGTH: 19
<212> TYPE: DNA
<213> ORGANISM: Artificial
<220> FEATURE:
<223> OTHER INFORMATION: Target Sequence

<400> SEQUENCE: 98
cacagagcct agacactga                                                    19

<210> SEQ ID NO 99
<211> LENGTH: 19
<212> TYPE: DNA
<213> ORGANISM: Artificial
<220> FEATURE:
<223> OTHER INFORMATION: Target Sequence

<400> SEQUENCE: 99
tccaagctct actccattg                                                    19

<210> SEQ ID NO 100
<211> LENGTH: 19
<212> TYPE: DNA
<213> ORGANISM: Artificial
<220> FEATURE:
<223> OTHER INFORMATION: Target Sequence

<400> SEQUENCE: 100
tggagctgtt ggtgggaat                                                    19

<210> SEQ ID NO 101
<211> LENGTH: 19
<212> TYPE: DNA
<213> ORGANISM: Artificial
<220> FEATURE:
<223> OTHER INFORMATION: Target Sequence

<400> SEQUENCE: 101
gacagggaga agagagata                                                    19

<210> SEQ ID NO 102
<211> LENGTH: 19
<212> TYPE: DNA
<213> ORGANISM: Artificial
<220> FEATURE:
<223> OTHER INFORMATION: Target Sequence

<400> SEQUENCE: 102
gggagaagag agatagtgt                                                    19

<210> SEQ ID NO 103
<211> LENGTH: 19
<212> TYPE: DNA
<213> ORGANISM: Artificial
<220> FEATURE:
<223> OTHER INFORMATION: Target Sequence
```

<400> SEQUENCE: 103
gagaagagag atagtgtgt                                                19

<210> SEQ ID NO 104
<211> LENGTH: 19
<212> TYPE: DNA
<213> ORGANISM: Artificial
<220> FEATURE:
<223> OTHER INFORMATION: Target Sequence

<400> SEQUENCE: 104
gaagagagat agtgtgtgt                                                19

<210> SEQ ID NO 105
<211> LENGTH: 19
<212> TYPE: DNA
<213> ORGANISM: Artificial
<220> FEATURE:
<223> OTHER INFORMATION: Target Sequence

<400> SEQUENCE: 105
gtgtgtgtcc ccaaggaaa                                                19

<210> SEQ ID NO 106
<211> LENGTH: 19
<212> TYPE: DNA
<213> ORGANISM: Artificial
<220> FEATURE:
<223> OTHER INFORMATION: Target Sequence

<400> SEQUENCE: 106
gaaaatatat ccaccctca                                                19

<210> SEQ ID NO 107
<211> LENGTH: 19
<212> TYPE: DNA
<213> ORGANISM: Artificial
<220> FEATURE:
<223> OTHER INFORMATION: Target Sequence

<400> SEQUENCE: 107
aaatatatcc accctcaaa                                                19

<210> SEQ ID NO 108
<211> LENGTH: 19
<212> TYPE: DNA
<213> ORGANISM: Artificial
<220> FEATURE:
<223> OTHER INFORMATION: Target Sequence

<400> SEQUENCE: 108
ctgtaccaag tgccacaaa                                                19

<210> SEQ ID NO 109
<211> LENGTH: 19
<212> TYPE: DNA
<213> ORGANISM: Artificial
<220> FEATURE:
<223> OTHER INFORMATION: Target Sequence

<400> SEQUENCE: 109
accaagtgcc acaaaggaa                                                19

<210> SEQ ID NO 110
<211> LENGTH: 19

<212> TYPE: DNA
<213> ORGANISM: Artificial
<220> FEATURE:
<223> OTHER INFORMATION: Target Sequence

<400> SEQUENCE: 110 ccaagtgccacaaaggaac                                                    19

<210> SEQ ID NO 111
<211> LENGTH: 19
<212> TYPE: DNA
<213> ORGANISM: Artificial
<220> FEATURE:
<223> OTHER INFORMATION: Target Sequence

<400> SEQUENCE: 111 ccacaaaggaacctacttg                                                    19

<210> SEQ ID NO 112
<211> LENGTH: 19
<212> TYPE: DNA
<213> ORGANISM: Artificial
<220> FEATURE:
<223> OTHER INFORMATION: Target Sequence

<400> SEQUENCE: 112
caaaggaacc tacttgtac                                                   19

<210> SEQ ID NO 113
<211> LENGTH: 19
<212> TYPE: DNA
<213> ORGANISM: Artificial
<220> FEATURE:
<223> OTHER INFORMATION: Target Sequence

<400> SEQUENCE: 113
aaaggaacct acttgtaca                                                   19

<210> SEQ ID NO 114
<211> LENGTH: 19
<212> TYPE: DNA
<213> ORGANISM: Artificial
<220> FEATURE:
<223> OTHER INFORMATION: Target Sequence

<400> SEQUENCE: 114
gatacggact gcagggagt                                                   19

<210> SEQ ID NO 115
<211> LENGTH: 19
<212> TYPE: DNA
<213> ORGANISM: Artificial
<220> FEATURE:
<223> OTHER INFORMATION: Target Sequence

<400> SEQUENCE: 115
cggactgcag ggagtgtga                                                   19

<210> SEQ ID NO 116
<211> LENGTH: 19
<212> TYPE: DNA
<213> ORGANISM: Artificial
<220> FEATURE:
<223> OTHER INFORMATION: Target Sequence

<400> SEQUENCE: 116

```
tccttcaccg cttcagaaa                                                19

<210> SEQ ID NO 117
<211> LENGTH: 19
<212> TYPE: DNA
<213> ORGANISM: Artificial
<220> FEATURE:
<223> OTHER INFORMATION: Target Sequence

<400> SEQUENCE: 117
cagaaaacca cctcagaca                                                19

<210> SEQ ID NO 118
<211> LENGTH: 19
<212> TYPE: DNA
<213> ORGANISM: Artificial
<220> FEATURE:
<223> OTHER INFORMATION: Target Sequence

<400> SEQUENCE: 118
tgcctcagct gctccaaat                                                19

<210> SEQ ID NO 119
<211> LENGTH: 19
<212> TYPE: DNA
<213> ORGANISM: Artificial
<220> FEATURE:
<223> OTHER INFORMATION: Target Sequence

<400> SEQUENCE: 119
ctccaaatgc cgaaaggaa                                                19

<210> SEQ ID NO 120
<211> LENGTH: 19
<212> TYPE: DNA
<213> ORGANISM: Artificial
<220> FEATURE:
<223> OTHER INFORMATION: Target Sequence

<400> SEQUENCE: 120 tccaaatgccgaaaggaaa                                                 19

<210> SEQ ID NO 121
<211> LENGTH: 19
<212> TYPE: DNA
<213> ORGANISM: Artificial
<220> FEATURE:
<223> OTHER INFORMATION: Target Sequence

<400> SEQUENCE: 121
ccaaatgccg aaaggaaat                                                19

<210> SEQ ID NO 122
<211> LENGTH: 19
<212> TYPE: DNA
<213> ORGANISM: Artificial
<220> FEATURE:
<223> OTHER INFORMATION: Target Sequence

<400> SEQUENCE: 122
gccgaaagga aatgggtca                                                19

<210> SEQ ID NO 123
<211> LENGTH: 19
<212> TYPE: DNA
<213> ORGANISM: Artificial
```

```
<220> FEATURE:
<223> OTHER INFORMATION: Target Sequence

<400> SEQUENCE: 123
aggaaatggg tcaggtgga                                                19

<210> SEQ ID NO 124
<211> LENGTH: 19
<212> TYPE: DNA
<213> ORGANISM: Artificial
<220> FEATURE:
<223> OTHER INFORMATION: Target Sequence

<400> SEQUENCE: 124
ggaaatgggt caggtggag                                                19

<210> SEQ ID NO 125
<211> LENGTH: 19
<212> TYPE: DNA
<213> ORGANISM: Artificial
<220> FEATURE:
<223> OTHER INFORMATION: Target Sequence

<400> SEQUENCE: 125
gtgtgtggct gcaggaaga                                                19

<210> SEQ ID NO 126
<211> LENGTH: 19
<212> TYPE: DNA
<213> ORGANISM: Artificial
<220> FEATURE:
<223> OTHER INFORMATION: Target Sequence

<400> SEQUENCE: 126
ggaagaacca gtaccggca                                                19

<210> SEQ ID NO 127
<211> LENGTH: 19
<212> TYPE: DNA
<213> ORGANISM: Artificial
<220> FEATURE:
<223> OTHER INFORMATION: Target Sequence

<400> SEQUENCE: 127
ccatgcaggt ttctttcta                                                19

<210> SEQ ID NO 128
<211> LENGTH: 19
<212> TYPE: DNA
<213> ORGANISM: Artificial
<220> FEATURE:
<223> OTHER INFORMATION: Target Sequence

<400> SEQUENCE: 128
catgcaggtt tctttctaa                                                19

<210> SEQ ID NO 129
<211> LENGTH: 19
<212> TYPE: DNA
<213> ORGANISM: Artificial
<220> FEATURE:
<223> OTHER INFORMATION: Target Sequence

<400> SEQUENCE: 129
tgcaggtttc tttctaaga                                                19
```

```
<210> SEQ ID NO 130
<211> LENGTH: 19
<212> TYPE: DNA
<213> ORGANISM: Artificial
<220> FEATURE:
<223> OTHER INFORMATION: Target Sequence

<400> SEQUENCE: 130
aggtttcttt ctaagagaa                                                19

<210> SEQ ID NO 131
<211> LENGTH: 19
<212> TYPE: DNA
<213> ORGANISM: Artificial
<220> FEATURE:
<223> OTHER INFORMATION: Target Sequence

<400> SEQUENCE: 131
ggtttctttc taagagaaa                                                19

<210> SEQ ID NO 132
<211> LENGTH: 19
<212> TYPE: DNA
<213> ORGANISM: Artificial
<220> FEATURE:
<223> OTHER INFORMATION: Target Sequence

<400> SEQUENCE: 132
agagaaaacg agtgtgtct                                                19

<210> SEQ ID NO 133
<211> LENGTH: 19
<212> TYPE: DNA
<213> ORGANISM: Artificial
<220> FEATURE:
<223> OTHER INFORMATION: Target Sequence

<400> SEQUENCE: 133
gagtgtgtct cctgtagta                                                19

<210> SEQ ID NO 134
<211> LENGTH: 19
<212> TYPE: DNA
<213> ORGANISM: Artificial
<220> FEATURE:
<223> OTHER INFORMATION: Target Sequence

<400> SEQUENCE: 134
ctgtagtaac tgtaagaaa                                                19

<210> SEQ ID NO 135
<211> LENGTH: 19
<212> TYPE: DNA
<213> ORGANISM: Artificial
<220> FEATURE:
<223> OTHER INFORMATION: Target Sequence

<400> SEQUENCE: 135
agaaaagcct ggagtgcac                                                19

<210> SEQ ID NO 136
<211> LENGTH: 19
<212> TYPE: DNA
<213> ORGANISM: Artificial
<220> FEATURE:
<223> OTHER INFORMATION: Target Sequence
```

```
<400> SEQUENCE: 136
ttgagaatgt taagggcac                                              19

<210> SEQ ID NO 137
<211> LENGTH: 19
<212> TYPE: DNA
<213> ORGANISM: Artificial
<220> FEATURE:
<223> OTHER INFORMATION: Target Sequence

<400> SEQUENCE: 137
tgttaagggc actgaggac                                              19

<210> SEQ ID NO 138
<211> LENGTH: 19
<212> TYPE: DNA
<213> ORGANISM: Artificial
<220> FEATURE:
<223> OTHER INFORMATION: Target Sequence

<400> SEQUENCE: 138
ggtcattttc tttggtctt                                              19

<210> SEQ ID NO 139
<211> LENGTH: 19
<212> TYPE: DNA
<213> ORGANISM: Artificial
<220> FEATURE:
<223> OTHER INFORMATION: Target Sequence

<400> SEQUENCE: 139
cctcctcttc attggttta                                              19

<210> SEQ ID NO 140
<211> LENGTH: 19
<212> TYPE: DNA
<213> ORGANISM: Artificial
<220> FEATURE:
<223> OTHER INFORMATION: Target Sequence

<400> SEQUENCE: 140
tcctcttcat tggtttaat                                              19

<210> SEQ ID NO 141
<211> LENGTH: 19
<212> TYPE: DNA
<213> ORGANISM: Artificial
<220> FEATURE:
<223> OTHER INFORMATION: Target Sequence

<400> SEQUENCE: 141
ctcttcattg gtttaatgt                                              19

<210> SEQ ID NO 142
<211> LENGTH: 19
<212> TYPE: DNA
<213> ORGANISM: Artificial
<220> FEATURE:
<223> OTHER INFORMATION: Target Sequence

<400> SEQUENCE: 142
tcttcattgg tttaatgta                                              19

<210> SEQ ID NO 143
```

```
<211> LENGTH: 19
<212> TYPE: DNA
<213> ORGANISM: Artificial
<220> FEATURE:
<223> OTHER INFORMATION: Target Sequence

<400> SEQUENCE: 143
cttcattggt ttaatgtat                                                  19

<210> SEQ ID NO 144
<211> LENGTH: 19
<212> TYPE: DNA
<213> ORGANISM: Artificial
<220> FEATURE:
<223> OTHER INFORMATION: Target Sequence

<400> SEQUENCE: 144
tccaagctct actccattg                                                  19

<210> SEQ ID NO 145
<211> LENGTH: 19
<212> TYPE: DNA
<213> ORGANISM: Artificial
<220> FEATURE:
<223> OTHER INFORMATION: Target Sequence

<400> SEQUENCE: 145
ctccattgtt tgtgggaaa                                                  19

<210> SEQ ID NO 146
<211> LENGTH: 19
<212> TYPE: DNA
<213> ORGANISM: Artificial
<220> FEATURE:
<223> OTHER INFORMATION: Target Sequence

<400> SEQUENCE: 146
gggaaatcga cacctgaaa                                                  19

<210> SEQ ID NO 147
<211> LENGTH: 19
<212> TYPE: DNA
<213> ORGANISM: Artificial
<220> FEATURE:
<223> OTHER INFORMATION: Target Sequence

<400> SEQUENCE: 147
tgaaggaact actactaag                                                  19

<210> SEQ ID NO 148
<211> LENGTH: 19
<212> TYPE: DNA
<213> ORGANISM: Artificial
<220> FEATURE:
<223> OTHER INFORMATION: Target Sequence

<400> SEQUENCE: 148
acctccagct ccacctata                                                  19

<210> SEQ ID NO 149
<211> LENGTH: 19
<212> TYPE: DNA
<213> ORGANISM: Artificial
<220> FEATURE:
<223> OTHER INFORMATION: Target Sequence

<400> SEQUENCE: 149
```
cccacaagcc acagagcct                                                    19

<210> SEQ ID NO 150
<211> LENGTH: 19
<212> TYPE: DNA
<213> ORGANISM: Artificial
<220> FEATURE:
<223> OTHER INFORMATION: Target Sequence

<400> SEQUENCE: 150
acgccgtggt ggagaacgt                                                    19

<210> SEQ ID NO 151
<211> LENGTH: 19
<212> TYPE: DNA
<213> ORGANISM: Artificial
<220> FEATURE:
<223> OTHER INFORMATION: Target Sequence

<400> SEQUENCE: 151
ggaaggaatt cgtgcggcg                                                    19

<210> SEQ ID NO 152
<211> LENGTH: 19
<212> TYPE: DNA
<213> ORGANISM: Artificial
<220> FEATURE:
<223> OTHER INFORMATION: Target Sequence

<400> SEQUENCE: 152
tgagcgacca cgagatcga                                                    19

<210> SEQ ID NO 153
<211> LENGTH: 19
<212> TYPE: DNA
<213> ORGANISM: Artificial
<220> FEATURE:
<223> OTHER INFORMATION: Target Sequence

<400> SEQUENCE: 153
gcgaggcgca atacagcat                                                    19

<210> SEQ ID NO 154
<211> LENGTH: 19
<212> TYPE: DNA
<213> ORGANISM: Artificial
<220> FEATURE:
<223> OTHER INFORMATION: Target Sequence

<400> SEQUENCE: 154
tgggctgcct ggaggacat                                                    19

<210> SEQ ID NO 155
<211> LENGTH: 19
<212> TYPE: DNA
<213> ORGANISM: Artificial
<220> FEATURE:
<223> OTHER INFORMATION: Target Sequence

<400> SEQUENCE: 155
catcaagtac tgaacgttt                                                    19

<210> SEQ ID NO 156
<211> LENGTH: 19
<212> TYPE: DNA

```
<213> ORGANISM: Artificial
<220> FEATURE:
<223> OTHER INFORMATION: Target Sequence

<400> SEQUENCE: 156
tcgtggtggt ggatggtaa                                              19

<210> SEQ ID NO 157
<211> LENGTH: 19
<212> TYPE: DNA
<213> ORGANISM: Artificial
<220> FEATURE:
<223> OTHER INFORMATION: Target Sequence

<400> SEQUENCE: 157
gaaagcgagt acactgtaa                                              19

<210> SEQ ID NO 158
<211> LENGTH: 19
<212> TYPE: DNA
<213> ORGANISM: Artificial
<220> FEATURE:
<223> OTHER INFORMATION: Target Sequence

<400> SEQUENCE: 158
gagcctgact ctagggttc                                              19

<210> SEQ ID NO 159
<211> LENGTH: 19
<212> TYPE: DNA
<213> ORGANISM: Artificial
<220> FEATURE:
<223> OTHER INFORMATION: Target Sequence

<400> SEQUENCE: 159
ccacataaga gatgatgat                                              19

<210> SEQ ID NO 160
<211> LENGTH: 19
<212> TYPE: DNA
<213> ORGANISM: Artificial
<220> FEATURE:
<223> OTHER INFORMATION: Target Sequence

<400> SEQUENCE: 160
cataagagat gatgatgtt                                              19

<210> SEQ ID NO 161
<211> LENGTH: 19
<212> TYPE: DNA
<213> ORGANISM: Artificial
<220> FEATURE:
<223> OTHER INFORMATION: Target Sequence

<400> SEQUENCE: 161
cgaatataac atagagcca                                              19

<210> SEQ ID NO 162
<211> LENGTH: 19
<212> TYPE: DNA
<213> ORGANISM: Artificial
<220> FEATURE:
<223> OTHER INFORMATION: Target Sequence

<400> SEQUENCE: 162
gttaatgata ccaaagaca                                              19
```

<210> SEQ ID NO 163
<211> LENGTH: 19
<212> TYPE: DNA
<213> ORGANISM: Artificial
<220> FEATURE:
<223> OTHER INFORMATION: Target Sequence

<400> SEQUENCE: 163
ctgaagatat caagaatgt                                                     19

<210> SEQ ID NO 164
<211> LENGTH: 19
<212> TYPE: DNA
<213> ORGANISM: Artificial
<220> FEATURE:
<223> OTHER INFORMATION: Target Sequence

<400> SEQUENCE: 164
atgaagagtt gctcccaaa                                                     19

<210> SEQ ID NO 165
<211> LENGTH: 19
<212> TYPE: DNA
<213> ORGANISM: Artificial
<220> FEATURE:
<223> OTHER INFORMATION: Target Sequence

<400> SEQUENCE: 165
atgaagaaca cgtgtaaat                                                     19

<210> SEQ ID NO 166
<211> LENGTH: 19
<212> TYPE: DNA
<213> ORGANISM: Artificial
<220> FEATURE:
<223> OTHER INFORMATION: Target Sequence

<400> SEQUENCE: 166
aattattggt ggtagcaga                                                     19

<210> SEQ ID NO 167
<211> LENGTH: 19
<212> TYPE: DNA
<213> ORGANISM: Artificial
<220> FEATURE:
<223> OTHER INFORMATION: Target Sequence

<400> SEQUENCE: 167
atcatcgctt ctacagata                                                     19

<210> SEQ ID NO 168
<211> LENGTH: 19
<212> TYPE: DNA
<213> ORGANISM: Artificial
<220> FEATURE:
<223> OTHER INFORMATION: Target Sequence

<400> SEQUENCE: 168
atacatgggc agaggggaa                                                     19

<210> SEQ ID NO 169
<211> LENGTH: 19
<212> TYPE: DNA
<213> ORGANISM: Artificial
<220> FEATURE:

```
<223> OTHER INFORMATION: Target Sequence

<400> SEQUENCE: 169
gggcagaggg gaagagagt                                                19

<210> SEQ ID NO 170
<211> LENGTH: 19
<212> TYPE: DNA
<213> ORGANISM: Artificial
<220> FEATURE:
<223> OTHER INFORMATION: Target Sequence

<400> SEQUENCE: 170
ggaagagagt acaactaca                                                19

<210> SEQ ID NO 171
<211> LENGTH: 19
<212> TYPE: DNA
<213> ORGANISM: Artificial
<220> FEATURE:
<223> OTHER INFORMATION: Target Sequence

<400> SEQUENCE: 171
gaagagagta caactacaa                                                19

<210> SEQ ID NO 172
<211> LENGTH: 19
<212> TYPE: DNA
<213> ORGANISM: Artificial
<220> FEATURE:
<223> OTHER INFORMATION: Target Sequence

<400> SEQUENCE: 172
gagagtacaa ctacaaatt                                                19

<210> SEQ ID NO 173
<211> LENGTH: 19
<212> TYPE: DNA
<213> ORGANISM: Artificial
<220> FEATURE:
<223> OTHER INFORMATION: Target Sequence

<400> SEQUENCE: 173
gctaattgac agagttgat                                                19

<210> SEQ ID NO 174
<211> LENGTH: 19
<212> TYPE: DNA
<213> ORGANISM: Artificial
<220> FEATURE:
<223> OTHER INFORMATION: Target Sequence

<400> SEQUENCE: 174
cggaacactt catgggata                                                19

<210> SEQ ID NO 175
<211> LENGTH: 19
<212> TYPE: DNA
<213> ORGANISM: Artificial
<220> FEATURE:
<223> OTHER INFORMATION: Target Sequence

<400> SEQUENCE: 175
ggataatgca ggttttaaa                                                19
```

```
<210> SEQ ID NO 176
<211> LENGTH: 19
<212> TYPE: DNA
<213> ORGANISM: Artificial
<220> FEATURE:
<223> OTHER INFORMATION: Target Sequence

<400> SEQUENCE: 176
aggctatgga atacagata                                                   19

<210> SEQ ID NO 177
<211> LENGTH: 19
<212> TYPE: DNA
<213> ORGANISM: Artificial
<220> FEATURE:
<223> OTHER INFORMATION: Target Sequence

<400> SEQUENCE: 177
gaatacagat agagcagat                                                   19

<210> SEQ ID NO 178
<211> LENGTH: 19
<212> TYPE: DNA
<213> ORGANISM: Artificial
<220> FEATURE:
<223> OTHER INFORMATION: Target Sequence

<400> SEQUENCE: 178
ggtaaaacct ggtgaaaag                                                   19

<210> SEQ ID NO 179
<211> LENGTH: 19
<212> TYPE: DNA
<213> ORGANISM: Artificial
<220> FEATURE:
<223> OTHER INFORMATION: Target Sequence

<400> SEQUENCE: 179
gtgaaaagca ctacaacat                                                   19

<210> SEQ ID NO 180
<211> LENGTH: 19
<212> TYPE: DNA
<213> ORGANISM: Artificial
<220> FEATURE:
<223> OTHER INFORMATION: Target Sequence

<400> SEQUENCE: 180
gaggaagcat ctaaagttt                                                   19

<210> SEQ ID NO 181
<211> LENGTH: 19
<212> TYPE: DNA
<213> ORGANISM: Artificial
<220> FEATURE:
<223> OTHER INFORMATION: Target Sequence

<400> SEQUENCE: 181
tatgggaact cttggatta                                                   19

<210> SEQ ID NO 182
<211> LENGTH: 19
<212> TYPE: DNA
<213> ORGANISM: Artificial
<220> FEATURE:
<223> OTHER INFORMATION: Target Sequence
```

```
<400> SEQUENCE: 182
tgacgagcac aaagaatta                                              19

<210> SEQ ID NO 183
<211> LENGTH: 19
<212> TYPE: DNA
<213> ORGANISM: Artificial
<220> FEATURE:
<223> OTHER INFORMATION: Target Sequence

<400> SEQUENCE: 183
gcacaaagaa ttatggtaa                                              19

<210> SEQ ID NO 184
<211> LENGTH: 19
<212> TYPE: DNA
<213> ORGANISM: Artificial
<220> FEATURE:
<223> OTHER INFORMATION: Target Sequence

<400> SEQUENCE: 184
ggttacaact catgaattg                                              19

<210> SEQ ID NO 185
<211> LENGTH: 19
<212> TYPE: DNA
<213> ORGANISM: Artificial
<220> FEATURE:
<223> OTHER INFORMATION: Target Sequence

<400> SEQUENCE: 185
actcatgaat tgggacata                                              19

<210> SEQ ID NO 186
<211> LENGTH: 19
<212> TYPE: DNA
<213> ORGANISM: Artificial
<220> FEATURE:
<223> OTHER INFORMATION: Target Sequence

<400> SEQUENCE: 186
gtggcgatca cgagaacaa                                              19

<210> SEQ ID NO 187
<211> LENGTH: 19
<212> TYPE: DNA
<213> ORGANISM: Artificial
<220> FEATURE:
<223> OTHER INFORMATION: Target Sequence

<400> SEQUENCE: 187
ctataagacc attgaaagt                                              19

<210> SEQ ID NO 188
<211> LENGTH: 19
<212> TYPE: DNA
<213> ORGANISM: Artificial
<220> FEATURE:
<223> OTHER INFORMATION: Target Sequence

<400> SEQUENCE: 188
gaacgcagca ataaagttt                                              19

<210> SEQ ID NO 189
<211> LENGTH: 19
```

```
<212> TYPE: DNA
<213> ORGANISM: Artificial
<220> FEATURE:
<223> OTHER INFORMATION: Target Sequence

<400> SEQUENCE: 189
gcaataaagt ttgtgggaa                                            19

<210> SEQ ID NO 190
<211> LENGTH: 19
<212> TYPE: DNA
<213> ORGANISM: Artificial
<220> FEATURE:
<223> OTHER INFORMATION: Target Sequence

<400> SEQUENCE: 190
caataaagtt tgtgggaac                                            19

<210> SEQ ID NO 191
<211> LENGTH: 19
<212> TYPE: DNA
<213> ORGANISM: Artificial
<220> FEATURE:
<223> OTHER INFORMATION: Target Sequence

<400> SEQUENCE: 191
gagggtggat gaaggagaa                                            19

<210> SEQ ID NO 192
<211> LENGTH: 19
<212> TYPE: DNA
<213> ORGANISM: Artificial
<220> FEATURE:
<223> OTHER INFORMATION: Target Sequence

<400> SEQUENCE: 192
ggatgaagga gaagagtgt                                            19

<210> SEQ ID NO 193
<211> LENGTH: 19
<212> TYPE: DNA
<213> ORGANISM: Artificial
<220> FEATURE:
<223> OTHER INFORMATION: Target Sequence

<400> SEQUENCE: 193
gcatcatgta tctgaacaa                                            19

<210> SEQ ID NO 194
<211> LENGTH: 19
<212> TYPE: DNA
<213> ORGANISM: Artificial
<220> FEATURE:
<223> OTHER INFORMATION: Target Sequence

<400> SEQUENCE: 194
caggaaatgc tgaagatga                                            19

<210> SEQ ID NO 195
<211> LENGTH: 19
<212> TYPE: DNA
<213> ORGANISM: Artificial
<220> FEATURE:
<223> OTHER INFORMATION: Target Sequence

<400> SEQUENCE: 195
```

```
gaatggcaaa tgtgagaaa                                                    19

<210> SEQ ID NO 196
<211> LENGTH: 19
<212> TYPE: DNA
<213> ORGANISM: Artificial
<220> FEATURE:
<223> OTHER INFORMATION: Target Sequence

<400> SEQUENCE: 196
ggatgtaatt gaacgattt                                                    19

<210> SEQ ID NO 197
<211> LENGTH: 19
<212> TYPE: DNA
<213> ORGANISM: Artificial
<220> FEATURE:
<223> OTHER INFORMATION: Target Sequence

<400> SEQUENCE: 197
gtggataaga aattggata                                                    19

<210> SEQ ID NO 198
<211> LENGTH: 19
<212> TYPE: DNA
<213> ORGANISM: Artificial
<220> FEATURE:
<223> OTHER INFORMATION: Target Sequence

<400> SEQUENCE: 198
ggataaacag tatgaatct                                                    19

<210> SEQ ID NO 199
<211> LENGTH: 19
<212> TYPE: DNA
<213> ORGANISM: Artificial
<220> FEATURE:
<223> OTHER INFORMATION: Target Sequence

<400> SEQUENCE: 199
cctttaaact gcagcgtca                                                    19

<210> SEQ ID NO 200
<211> LENGTH: 19
<212> TYPE: DNA
<213> ORGANISM: Artificial
<220> FEATURE:
<223> OTHER INFORMATION: Target Sequence

<400> SEQUENCE: 200
cgtgttgaca gcaaagaaa                                                    19

<210> SEQ ID NO 201
<211> LENGTH: 19
<212> TYPE: DNA
<213> ORGANISM: Artificial
<220> FEATURE:
<223> OTHER INFORMATION: Target Sequence

<400> SEQUENCE: 201
gcaaagaaac agagtgcta                                                    19

<210> SEQ ID NO 202
<211> LENGTH: 19
<212> TYPE: RNA
<213> ORGANISM: Artificial
```

```
<220> FEATURE:
<223> OTHER INFORMATION: Target Sequence

<400> SEQUENCE: 202
caaaggaacc uacuuguac                                                    19

<210> SEQ ID NO 203
<211> LENGTH: 19
<212> TYPE: RNA
<213> ORGANISM: Artificial
<220> FEATURE:
<223> OTHER INFORMATION: Target Sequence

<400> SEQUENCE: 203
gagcuugaag gaacuacua                                                    19

<210> SEQ ID NO 204
<211> LENGTH: 19
<212> TYPE: RNA
<213> ORGANISM: Artificial
<220> FEATURE:
<223> OTHER INFORMATION: Target Sequence

<400> SEQUENCE: 204
cacagagccu agacacuga                                                    19

<210> SEQ ID NO 205
<211> LENGTH: 19
<212> TYPE: RNA
<213> ORGANISM: Artificial
<220> FEATURE:
<223> OTHER INFORMATION: Target Sequence

<400> SEQUENCE: 205
uccaagcucu acuccauug                                                    19
```